United States Patent
Serraïma et al.

(10) Patent No.: US 9,315,564 B2
(45) Date of Patent: Apr. 19, 2016

(54) COSMETIC OR PHARMACEUTICAL COMPOSITIONS COMPRISING METALLOPROTEINASE INHIBITORS

(75) Inventors: Cristina Carreño Serraïma, Barcelona (ES); Wim Van Den Nest, Vilanova I La Geltru-Barcelona (ES); Juan Cebriàn Puche, Barcelona (ES); Nuria Almiñana Domenech, Barcelona (ES); Antonio Ferrer Montiel, Alicante (ES); Nuria Garcia Sanz, El Campello (ES)

(73) Assignee: Lipotec, S.A., Gava, Barcelona (ES)

( * ) Notice: Subject to any disclaimer, the term of this patent is extended or adjusted under 35 U.S.C. 154(b) by 1327 days.

(21) Appl. No.: 12/920,241

(22) PCT Filed: Feb. 27, 2009

(86) PCT No.: PCT/EP2009/001419
§ 371 (c)(1),
(2), (4) Date: Sep. 17, 2010

(87) PCT Pub. No.: WO2009/106343
PCT Pub. Date: Sep. 3, 2009

(65) Prior Publication Data
US 2011/0002969 A1    Jan. 6, 2011

(30) Foreign Application Priority Data

Feb. 29, 2008  (ES) .................................. 200800597

(51) Int. Cl.
| | | |
|---|---|---|
| C07K 14/81 | (2006.01) | |
| A61K 8/64 | (2006.01) | |
| A61K 9/00 | (2006.01) | |
| A61K 9/06 | (2006.01) | |
| A61K 9/127 | (2006.01) | |
| A61Q 7/00 | (2006.01) | |
| A61Q 19/06 | (2006.01) | |
| A61Q 19/08 | (2006.01) | |
| C07K 5/11 | (2006.01) | |
| A61K 38/00 | (2006.01) | |
| A61Q 5/00 | (2006.01) | |

(52) U.S. Cl.
CPC ............... *C07K 14/8146* (2013.01); *A61K 8/64* (2013.01); *A61K 9/0014* (2013.01); *A61K 9/06* (2013.01); *A61K 9/127* (2013.01); *A61Q 7/00* (2013.01); *A61Q 19/06* (2013.01); *A61Q 19/08* (2013.01); *C07K 5/1019* (2013.01); *A61K 38/00* (2013.01); *A61Q 5/00* (2013.01)

(58) Field of Classification Search
None
See application file for complete search history.

(56) References Cited

U.S. PATENT DOCUMENTS

| 6,303,752 | B1 * | 10/2001 | Olsen et al. ................... 530/350 |
| 7,642,079 | B2 * | 1/2010 | Cayouette et al. ............ 435/212 |
| 2003/0148959 | A1 * | 8/2003 | Quirk et al. ..................... 514/15 |
| 2003/0166567 | A1 * | 9/2003 | Quirk et al. ..................... 514/14 |
| 2004/0127420 | A1 * | 7/2004 | Quirk .............................. 514/13 |
| 2011/0002969 | A1 * | 1/2011 | Serraima et al. .............. 424/401 |

FOREIGN PATENT DOCUMENTS

| WO | 9808815 | | 3/1998 |
| WO | 9836742 | | 8/1998 |
| WO | 9900489 | * | 1/1999 |
| WO | 9958101 | | 11/1999 |
| WO | 03016520 | * | 2/2003 |
| WO | 04033668 | * | 4/2004 |
| WO | 2004033668 | | 4/2004 |

OTHER PUBLICATIONS

Dweck. R.G. Harry Cosmeticology 8th edition, 2000, 27 Pages, "Botanicals in Cosmetics & Toiletries."
Gottschalck et al. International Cosmetic Ingredient Dictionary and Handbook, 12th edition 2008, vol. 3, 14 Pages, "Biological Polymers and their Derivatives (Including salts, excluding gums, hydrophilic colloids and derivatives)."
Abraham et al. Current Vascular Pharmacology 2005, vol. 3, p. 369-379, "Connective Tissue Remodeling: Cross-Talk between Endothelins and Matrix Metalloproteinases."
Miyoshi et al. The Journal of Dermatology 2005, vol. 32, p. 346-353, "Beneficial Effects of Tissue Inhibitor of Metalloproteinases-2 (TIMP-2) on Chronic Dermatitis."
Duivenvoorden et al. Invasion Metastasis 1997, vol. 17, p. 312-322, "Use of Tetracycline as an Inhibitor of Matrix Metalloproteinase Activity Secreted by Human Bone-Metastasizing Cancer Cells."
Su et al. Hybridoma 1995, vol. 14, No. 4, p. 383-390 "Monoclonal Antibodies against Human Collagenase and Stromelysin."
Smith et al. 1999, 5th edition, 111 Pages, "March's Advanced Organic Chemistry Reactions, Mechanisms, and Structure."
Remington, 21st edition, 2005, "The Science and Practice of Pharmacy." 60 Pages.
Reynolds et al. J. R. Coll. Surg. Edinb. Jun. 1997, vol. 42, p. 154-160, "The functional balance of metalloproteinases and inhibitors in tissue degradation: relevance to oral pathologies."
Fauli. Treated Galenic Pharmacy 1993, "Pharmaceutical Technology", English translation of first paragraph, 8 Pages.

(Continued)

*Primary Examiner* — Maury Audet
(74) *Attorney, Agent, or Firm* — Fay Sharpe LLP

(57) ABSTRACT

Peptides of general formula (I): $R_1AA_1-AA_2-AA_3-AA_4-R_2$ stereoisomers thereof, mixtures thereof or the cosmetically or pharmaceutically acceptable salts thereof, a method for obtaining them, cosmetic or pharmaceutical compositions containing them, and their use for the treatment and/or care of those conditions, disorders and/or pathologies of the skin, mucosae and/or scalp resulting from matrix metalloproteinases (MMP) overexpression or an increase in the MMP activity.

20 Claims, No Drawings

(56) References Cited

OTHER PUBLICATIONS

Miyazaki et al. Seikagaku 1996, vol. 68, No. 12, p. 1791-1807, English Abstract attached to original document, "Matrix metalloproteinases. Their structures and functions, with special reference to their roles in tumor invasion and metastasis."
Remington., Remingtons Pharmaceutical Sciences 1965, English abstract attached to original document, All together 8 Pages, "Remingtons Practice of Pharmacy.".
Wiberg et al. "Complexes of Matrilin-1 and Biglycan or Decorin Connect Collagen VI Microfibrils to Both Collagen II and Aggrecan", The Journal of Biological Chemistry, Issue of Sep. 26, 2002, vol. 278, No. 39, p. 37698-37704.
Kullmann. "Proteases as Catalysts for Enzymic Syntheses of Opioid Peptides", The Journal of Biological Chemistry Issue of Sep. 10, 1980, vol. 255, No. 17, p. 8234-8238.
Scott. "Elasticity in Extracellular Matrix "Shape Modules" of Tendon, Cartilage, etc. A Sliding Proteoglycan-Filament Model", J. Physiol. 2003, vol. 553, No. 2, p. 335-343.
Woessner, Jr. "Matrix Metalloproteinases and Their Inhibitors in Connective Tissue Remodeling", The FASEB Journal, May 1991, vol. 5, p. 2145-2154.
Suomela et al. "Matrix Metalloproteinase-19 is Expressed by Keratinocytes in Psoriasis", Acta. Derm. Venereol. 2003, vol. 83, p. 108-114.
Kerkela et al. "Matrix Metalloproteinases in Tumor Progression: Focus on Basal and Squamous Cell Skin Cancer", Experimental Dermatology 2003, vol. 12, p. 109-125.
Sato et al. "Roles of Membrane-type Matrix Metalloproteinase-1 in Tumor Invasion and Metastasis", Cancer Sci., Apr. 2005, vol. 96, No. 4, p. 212-217.
Fisher et al. "Pathophysiology of Premature Skin Aging Induced by Ultraviolet Light", New Eng. J. Med. 1997, vol. 337, No. 20, p. 1419-1429.
Traurig et al. "Differential Expression of Matrix Metalloproteinase 3 (MMP3) in Preadipocytes/Stromal Vascular Cells From Nonobese Nondiabetic Versus Obese Nondiabetic Pima Indians", Diabetes, Nov. 2006, vol. 55, p. 3160-3165.
Kahari et al. "Matrix Metallproteinases in Skin", Exp. Dermatol. 1997, vol. 6, p. 199-213.
Papakonstantinou et al. "Matrix Metallpproteinases of Epithelial Origin in Facial Sebum of Patients with Acne and their Regulation by Isotretinoin", J. Invest Dermatol. 2005, vol. 125, p. 673-684.
Fisher et al. "Ultraviolet Irradiation Increases Matrix Metalloproteinase-8 Protein in Human Skin in Vivo", J. Invest. Dermatol. 2001, vol. 117, p. 219-226.
Ntayi et al. "Implication of Matrix Metalloproteinases (MMPs) in Cutaneous Melanoma Progression", Pathologie Biologie 2004, vol. 52, p. 154-159.
Rittie et al. "UV-Light-Induced Signal Cascades and Skin Aging", Ageing Research Reviews 2002, vol. 1, p. 705-720.
Lahmann et al. "Matrix Metalloproteinase-1 and Skin Ageing in Smokers", The Lancet, Mar. 24, 2001, vol. 357, p. 935-936.
Sapadin et al. "Tetracyclines: Nonantibiotic Properties and Their Clinical Implications", J. Am. Acad. Dem. 2006, vol. 54, p. 258-265.
Herouy et al. "Inflammation in Stasis Dermatitis Upregulates MMP-1, MMp-2 and MMP-13 Expression", Journal of Dermatological Science 2001, vol. 25, p. 198-205.
Demeulemeester et al. "Effect of Matrix Metalloproteinase Inhibition on Adipose Tissue Development", Biochemical and Biophysical Research Communications 2005, vol. 329, p. 105-110.
Odake et al. "Inhibition of Matrix Metalloproteinases by Peptidyl Hydroxamic Acids", Biochemical and Biophysical Research Communications, Mar. 30, 1994, vol. 199, No. 3, p. 1442-1446.
Lloyd-Williams et al. "Tetragedron Report No. 347: Convergent Solid-Phase Peptide Synthesis", Tetrahedron 1993, V01.49, No. 48, p. 11065-11133.
Barlos et al. "Darstellung Geschutzter Peptide-Fragmente Unter Einsatz Substituierter Triphenylmethyl-Harze", Tetrahedron Letters 1989, vol. 30, No. 30, p. 3943-3946.
Barlos et al. "Veresterung Von Partiell Geschutzten Peptid-Fragmenten Mit Harzen. Einsatz Von @-Chlortritylchlorid Zur Synthese Von Leu—Gastrin 1", Tetrahedron Letters 1989, vol. 30, No. 30, p. 3947-3950.
Schaab et al. "Impregnating Fabrics With Microcapsules", HAPPI May 1986, p. 84-86.
Nelson. "Application of Microencapsulation in Textiles", International Journal of Pharmaceutics 2002, vol. 242, p. 55-62.
Malcolm et al. "Controlled Release of Model Antibacterial Drug From a Novel Self-Lubricating Silicone Biomaterial", Journal of Controlled Release 2004, vol. 97, p. 313-320.
Aumailley et al. "Structure and Biological Activity of the Extracellular Matrix", J. Mol. Med. 1998, vol. 76, p. 253-265.
Flisiak et al. "Effect of Psoriasis Treatment on Plasma Concentrations of Metalloproteinase-1 and Tissue Inhibitor of Metalloproteinases-1", Journal of the European Academy of Dermatology and Venereology 2005, vol. 19, p. 418-421.
Devillers et al. "Elevated Levels of Plasma Matrix Metalloproteinase-9 in Patients with Atopic Dermatitis: A Pilot Study", Clinical and Experimental Dermatology 2007, vol. 32, p. 311-313.
Jarousse et al. "Identification of Clustered Cells in Human Hair Follicle Responsible for MMP-9 Gelatinolytic Activity: Consequences for the Regulation of Hair Growth", International Journal of Dermatology 2001, vol. 40, p. 385-392.
Wojtowicz-Praga et al. "Matrix Metalloproteinase Inhibitors" Investigational New Drugs 1997, vol. 15, p. 61-75.
Albericio et al. "Preparation and Application of the 5-(4-(9-Flyorenylmethyloxycarbonyl)Aminomethy1-3,5-Dimethoxyphenoxy)-Valeric Acid (PAL) Handle for the Solid-Phase Synthesis of C-Terminal Peptide Amides Under Mild Conditions 1-3", J. Org. Chem. 1990, vol. 55, p. 3730-3743.
Culav et al. "Connective Tissues:Matrix Composition and Its Relevance to Physical Therapy." Physical Therapy Mar. 1999, vol. 79, No. 3, p. 308-319.
Matsueda et al. "A p-Methylbenzhydrylamine Resin for Improved Solid-Phase Synthesis of Peptide Amides." Peptides 1981, vol. 2, p. 45-50.
Bodanszky et al. "The Practice of Peptide Synthesis." The Practice of Peptide Synthesis 1984 Second, Revised Edition, 54 Pages.
Greene et al. "Protective Groups in Organic Synthesis." Protective Groups in Organic Synthesis 1999, Third Edition, 20 Pages.
Atherton et al. "Solid phase peptide synthesis." Oxford University Press 1989, 17 Pages.
Wang. "p-Alkoxybenzyl Alcohol Resin and p-Alkoxybenzyloxycarbonylhydrazide Resin for Solid Phase Syntheis of Protected Peptide Fragements." Journal of the American Chemical Society Feb. 21, 1973, vol. 95, p. 1328-1333.
International Search Report for PCT/EP2009/001419, Completed by the European Patent Office on Jun. 8, 2009, 2 Pages.
Berge et al. "Review Article, Pharmaceutical Salts." Journal of Pharmaceutical Sciences Jan. 1977, vol. 66, No. 1, p. 1-19.
Elsner. "Antimicrobials and the Skin Physiological and Pathological Flora." Curr Probl Dermatol. 2006, vol. 33, p. 35-41.
Haug et al. "Coated Textiles in the Treatment of Atopic Dermatitis." Curr Probl Dermatol. 2006, vol. 33, p. 144-151.
Freinkel et al. The Biology of Skin 2001, p. 32-35, "Structure and Function of the Skin: Overview of the Epidermis and Dermis."
Lloyd-Williams et al. "Chemical Approaches to the Synthesis of Peptides and Proteins." Chemical Approaches to the Synthesis of Peptides and Proteins 1997, 78 Pages.
Kaiser et al. "Color Test for Detection of Free Terminal Amino Groups in the Solid-Phase Synthesis of Peptides." Anal Biochem 1970, vol. 34, p. 595-398.
Dixon et al. "Nomenclature and Symbolism for Amino Acids and Peptides." Eur J. Biochem. 1984, vol. 138, p. 9-37.
Levy et al. "Matrix Metalloproteinase Inhibitors: A Structure—Activity Study." J. Med. Chem. 1998, vol. 41, p. 199-223.
Fisher et al. "Molecular basis of sun-induced premature skin ageing and retinoid antagonism." Nature Jan. 1996, vol. 379, p. 335-339.
Stewart et al. "Solid Phase Peptide Synthesis." Solid Phase Peptide Synthesis Nov. 1984, Second Edition, 20 Pages.

* cited by examiner

```
                        SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Xaa is Cit
<220> FEATURE:
<221> NAME/KEY: MISC_FEATURE
<223> OTHER INFORMATION: Xaa is Cit
<220> FEATURE:
<221> NAME/KEY: MISC_FEATURE
<223> OTHER INFORMATION: Sequence is synthesized
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Arg His His Xaa
1

<210> SEQ ID NO 2
<211> LENGTH: 4
<212> TYPE: PRT
<213> ORGANISM: Artificial Sequence
<220> FEATURE:
<223> OTHER INFORMATION: Xaa is Cit
<220> FEATURE:
<221> NAME/KEY: MISC_FEATURE
<223> OTHER INFORMATION: Xaa is Cit
<220> FEATURE:
<221> NAME/KEY: MISC_FEATURE
<223> OTHER INFORMATION: Sequence is synthesized
<220> FEATURE:
<221> NAME/KEY: misc_feature
<222> LOCATION: (4)..(4)
<223> OTHER INFORMATION: Xaa can be any naturally occurring amino acid
```

```
<400> SEQUENCE: 2

Arg Asn Arg Xaa
1

<210> SEQ ID NO 3
<211> LENGTH: 4
<212> TYPE: PRT
<213> ORGANISM: Artificial Sequence
<220> FEATURE:
<223> OTHER INFORMATION: Xaa is Cit
<220> FEATURE:
<221> NAME/KEY: MISC_FEATURE
<223> OTHER INFORMATION: Xaa is Cit
<220> FEATURE:
<221> NAME/KEY: MISC_FEATURE
<223> OTHER INFORMATION: Sequence is synthesized
<220> FEATURE:
<221> NAME/KEY: misc_feature
<222> LOCATION: (4)..(4)
<223> OTHER INFORMATION: Xaa can be any naturally occurring amino acid

<400> SEQUENCE: 3

Arg Asn His Xaa
1

<210> SEQ ID NO 4
<211> LENGTH: 4
<212> TYPE: PRT
<213> ORGANISM: Artificial Sequence
<220> FEATURE:
<223> OTHER INFORMATION: Xaa is Cit
<220> FEATURE:
<221> NAME/KEY: MISC_FEATURE
<223> OTHER INFORMATION: Xaa is Cit
<220> FEATURE:
<221> NAME/KEY: MISC_FEATURE
<223> OTHER INFORMATION: Sequence is synthesized
<220> FEATURE:
<221> NAME/KEY: misc_feature
<222> LOCATION: (4)..(4)
<223> OTHER INFORMATION: Xaa can be any naturally occurring amino acid

<400> SEQUENCE: 4

Arg His Arg Xaa
1
```

COSMETIC OR PHARMACEUTICAL COMPOSITIONS COMPRISING METALLOPROTEINASE INHIBITORS

FIELD OF THE INVENTION

The present invention refers to peptides capable of inhibiting the activity of matrix metalloproteinases (MMP) and to cosmetic or pharmaceutical compositions containing such peptides which can be used in the treatment and/or care of skin, mucosae and/or to scalp, preferably for the treatment and/or care of those conditions, disorders and/or pathologies of skin, mucosae and/or scalp resulting from MMP overexpression or an increase in the MMP activity.

BACKGROUND OF THE INVENTION

The skin is made up of two layers: epidermis and dermis. The outer layer is the epidermis which is made up mainly of keratinocytes, melanocytes and Langerhans cells and its basic function is to retain body water, act as a barrier against harmful chemical agents as well as against pathogen agents, and perform cellular renovation processes. The inner layer, dermis, formed by fibroblasts, adipocytes and macrophages is tightly connected to the epidermis through the basal membrane and it contains numerous nerve endings which provide tactile and temperature sensations. It also houses hair follicles, sweat glands, sebaceous glands, Apocrine Glands and blood vessels, and one of its main functions is to keep the skin elasticity and appearance.

The dermis also includes the extracellular matrix, formed by a group of extracellular proteins (fibrous proteins, glycoproteins and proteoglycans) whose principal function is to keep skin structure. Correct tissue functioning and development depend on the right formation of the extracellular matrix and on the right regulation of its components [Wiberg C., Klatt A. R., Wagener R., Paulsson M., Bateman J. F., Heinegard D. and Morgelin M. (2003) "*Complexes of matrilin-1 and biglycan or decorin connect collagen VI microfibrils to both collagen II and aggrecan*" *J. Biol. Chem.* 278:37698-37704]. The two most important fibrous proteins in the extracellular matrix are collagen and elastin, which are responsible for the mechanical properties of the tissues such as the ability to resist tension, compression, extensibility and torsion. Proteoglycans have a structural and metabolic function, while glycoproteins, together with proteoglycans, work as a union bridge between matrix components and cells [Aumailley M. and Gayraud B. (1998) "*Structure and biological activity of the extracellular matrix*" *J. Mol. Med.* 76:253-265; Culav E. M., Clark C. H. and Merrilees M. J. (1999) "*Connective tissues: matrix composition and its relevance to physical therapy*" *Phys. Ther.* 79:308-319; Scott J. E. (2003) "*Elasticity in extracellular matrix 'shape modules' of tendon, cartilage, etc. A sliding proteoglycan-filament model*" *J. Physiol.* 553:335-343].

Collagens are a family of fibrous proteins of the extracellular matrix that constitute a 25% of the total proteic mass in mammals. They have been classified in more than 20 families, all of them having individual characteristics which fulfill specific functions in different tissues.

The main characteristic of collagen is its helicoidal structure formed by the association of three polypeptide chains rich in glycine and proline. Alterations in its aminoacid composition cause dysfunction and loss of its mechanical properties [Culav E. M., Clark C. H. and Merrilees M. J. (1999) "*Connective tissues: matrix composition and its relevance to physical therapy*" *Phys. Ther.* 79:308-319]. These polypeptide chains can associate one to the other and form fibrils, which have a diameter of 10-300 nm and a length of up to hundreds of micrometers in mature tissues. These fibrils are often added into major structures, such as cable bunching, which can be seen through electronic microscopy as collagen fibers of many micrometers in diameter. This process is known as fibrillogenesis [Aumailley M. and Gayraud B. (1998) "*Structure and biological activity of the extracellular matrix*" *J. Mol. Med.* 76:253-265]. Not all collagens have the ability to form fibrils; only I, II, III, V and XI type collagens, which are known as fibrillar collagens.

An adult dermis is basically formed by fibrillar collagens type I, III and V. Type I collagens represent 80-90% of the total collagen of the dermis. Generally, type I collagen fibers feature a bigger diameter, which correlates with its ability to withstand a bigger mechanical load. Type III collagen intervenes in tissue extensibility, and as years go by, it is replaced by type I collagen molecules, process which is partly responsible for mature skins being less extensible than young skins. Type V collagen associates with types I and III regulating the diameter of fibrils ["*The Biology of the Skin*", Freinkel R. K. and Woodley D. T, eds. The Parthenon Publishing Group, 2001; Culav E. M., Clark C. H. and Merrilees M. J. (1999) "*Connective tissues: matrix composition and its relevance to physical therapy*" *Phys. Ther.* 79:308-319].

Collagen fibers are in constant renewal process, but such renewal decreases with age, causing the thinning of dermis. Besides, even though collagen fibers organization provides collagen network with great resistance, collagen fibers are sensitive to certain enzymes known as matrix metalloproteases (MMP). MMPs belong to a family of proteolytic enzymes (endoproteases) which contain a zinc atom coordinated with three cysteine residues and one residue of methionine in its active center and which can, collectively, degrade macromolecular components from the extracellular matrix and from the basal laminas into a neutral pH (collagen, elastin, etc.).

The family of matrix metalloproteases is classified according to its structural similarity and its substrate specificity [Woessner J. F. (1991) "*Matrix metalloproteinases and their inhibitors in connective tissue remodeling*" *Faseb J.* 5:2145-2154; Miyazaki K. and Higashi S. (1996) "*Matrix metalloproteinases: their structures and functions, with special reference to their roles in tumor invasion and metastasis*" *Seikagaku* 68:1791-1807]. Within the family of MMPs there are collagenases which degrade fibrilar collagen (MMP-1 or interstitial collagenase, MMP-8 or neutrophil collagenase, MMP-3 or collagenase 3), gellatinases which degrade type IV collagen or any other form of denaturalized collagen (MMP-2 or gellatinase A 72 kDa and MMP-9 or gellatinase B 92 kDa), stromelysins whose wide spectrum of activity is directed to the extracellular matrix proteins such as glycoproteins like fibronectin or laminin and proteoglycans, among others (MMP-3 or stromelysin 1, MMP-10 or stromelysin 2 and MMP-11 or stromelysin 3), matrilysin (MMP-7) metalloelastase (MMP-12) or the membrane metalloproteases (MMP-14, MMP-15, MMP-16 and MMP-17).

Metalloproteases are produced and secreted in an inactive way (proenzyme), which is later activated in the extracellular environment by the loss of the propeptide region of its sequence. The members of this protein family can activate one another. The MMP activity regulation can take place in different ways: regulating gens expression (transcription and transfer), regulating inactive process activation or acting locally on the active process.

MMPs play an important role in different skin, mucosae and/or scalp conditions and disorders in which there is a degradation and destruction of extracellular proteins [Kahari V. M. and Saarialho-Kere U. (1997) "*Matrix metalloproteinases in skin*" *Exp. Dermatol.* 6:199-213]. Among the different pathologies described in which there is a MMP overexpression or an increase of MMP activity in connective tissue cells, we find chronic ulcer [Miyoshi H., Kanekura T., Aoki T. and Kanzaki T. (2005) "*Beneficial effects of tissue inhibitor of metalloproteinases-2 (TIMP-2) on chronic dermatitis*" *J. Dermatol.* 32:346-353], psoriasis [Flisiak I., Mysliwiec H. and Chodynicka B. (2005) "*Effect of psoriasis treatment on plasma concentrations of metalloproteinase-1 and tissue inhibitor of metalloproteinase-1*" *J. Eur. Acad. Dermatol. Venereol.* 9:418-421; Suomela S., Kariniemi A. L., Impola U., Karvonen S. L., Snellman E., Uurasmaa T., Peltonen J., Saarialho-Kere U. (2003) "*Matrix metalloproteinase-19 is expressed by keratinocytes in psoriasis*" *Acta Derm. Venereol.* 83:108-114], oral pathologies such as gingivitis and periodontitis [Reynolds J. J. and Meikle M. C. (1997) "*The functional balance of metalloproteinases and inhibitors in tissue degradation: relevance to oral pathologies*" *J. R. Coll. Surg. Edinb.* 42:154-160], skin cancer [Ntayi C., Hornebeck W and Bernard P. (2004) "*Involvement of matrix metalloproteinases (MMPs) in cutaneous melanoma progression*" *Pathol. Biol.* (Paris) 52:154-159; Kerkela E. and Saarialho-Kere U. (2003) "*Matrix metalloproteinases in tumor progression: focus on basal and squamous cell skin cancer*" *Exp. Dermatol.* 12:109-125] and tumor invasion and metastasis [Sato H., Takino T. and Miyamori H. (2005) "*Roles of membrane-type matrix metalloproteinase-1 in tumor invasion and metastasis*" *Cancer Sci.* 96:212-217].

MMPs also play a key role in different physiological situations in which the extracellular matrix is degraded or reconstructed, such as the extracellular matrix proteolytic remodeling, including tissue morphogenesis during development, tissue repair and angiogenesis [Kahari V. M. and Saarialho-Kere U. (1997) "*Matrix metalloproteinases in skin*" *Exp. Dermatol.* 6:199-213]. In a particular way, MMPs have a crucial role in connective tissue remodeling [Abraham D., Ponticos M. and Nagase H. (2005) "*Connective tissue remodeling: cross-talk between endothelins and matrix metalloproteinases*" *Curr. Vasc. Pharmacol.* 3:369-379], for example collagen degradation by MMPs makes the skin look wrinkled and flaccid.

Likewise, MMPs participate in skin aging. Different factors, including exposure to ultraviolet (UV) radiation, produce collagen degradation, with all the consequences it entails on skin structure and/or firmness, particularly on those skin areas exposed to the solar light such as the face, ears, neck, scalp, arms and hands.

Skin damage associated to chronic exposition (repetitive irradiation) or high exposition (strong irradiation) to UVA and/or UVB rays has been studied; particularly it is known that UVB rays (290-300 nm; 5% of total UV rays) with more energetic wavelength, especially affect epidermic cells (keratinocytes) acting over its DNA.

UVA rays (320-400 nm; 95% of total UV rays) have a stronger penetration grade and also act over dermic cells such as fibroblasts and they act indirectly generating free radicals.

Moreover, prolonged exposure to UV radiation, particularly to UVA and/or UVB radiation stimulates MMP expression [Fisher G. J., Datta S. C., Talwar H. S., Wang Z. Q., Varani J., Kang S. and Voorhees J. J. (1996) "*Molecular basis of sun-induced premature skin ageing and retinoid antagonism*" *Nature* 379:335-339; Fisher G. J., Wang Z. Q., Datta S. C., Varani J., Kang S. and Voorhees J. J. (1997) "*Pathophysiology of Premature Skin Aging Induced by Ultraviolet Light*" *New Eng. J. Med.* 337:14191429; Fisher G. J., Choi H. C., Bata-Csorgo Z., Shao Y, Datta S., Wang Z. Q., Kang S. and Voorhees J. J. (2001) "*Ultraviolet irradiation increases matrix metalloproteinase-8 protein in human skin in vivo*" *J. Invest. Dermatol.* 117:219-226], especially matrix metalloelastase type 1 (MMP-1). This is one of the components of photoinduced skin aging (or photoaging) [Rittie L. and Fisher G. J. (2002) "*UV-light-induced signal cascades and skin aging*" *Ageing Res. Rev.* 1:705-720]. Besides, it is known that MMP-1, MMP-2 and MMP-9 activity increases with age and that this increase, together with cell growth deceleration, contributes to chronologic skin aging [EP 1 005 333 B1]. Similarly, smokers' skin also has a premature aging aspect in which MMPs are overexpressed [Lahmann C., Bergemann J., Harrison G. and Young A. R. (2001) "*Matrix metalloproteinase-1 and skin aging in smokers*" *Lancet* 357:935-936].

Another skin and/or scalp pathologies or disorders, associated to MMP overexpression or to an increase of MMP activity in the connective tissue is acne [Papakonstantinou E., Aletras A. J., Glass E., Tsogas P., Dionyssopoulos A., Adjaye J., Fimmel S., Gouvousis P., Herwig R., Lehrach H., Zouboulis C. C. and Karakiulakis G. (2005) "*Matrix metalloproteinases of epithelial origin in facial sebum of patients with acne and their regulation by isotretinoin*" *J. Invest. Dermatol.* 125:673-684]. It is described that skins affected by acne have high levels of MMP-1.

Likewise, rosacea is a skin and/or scalp pathology or disorder in which MMPs are also involved. Rosacea is characterized by an increase of angiogenesis and inflammation. Angiogenesis refers to the process of new blood vessels formation and it includes benign conditions such as rosacea and malignant processes such as cancer. Matrix degrading enzymes, present in tissue extracellular matrix facilitate angiogenesis since they allow new blood vessels to penetrate the matrix. MMPs represent a kind of enzymes involved in such processes [Sapadin A. N., Fleischmajer R. (2006) "*Tetracyclines: Nonantibiotic properties and their clinical implications*" *J. Am. Acad. Derm.* 54:258-265].

People with dermatitis, including contact dermatitis and atopic dermatitis, also have high levels of some MMPs [Herouy Y, Mellios P., Bandemir E., Dichmann S., Nockowski P., Schöpf E. and Norgauer J. (2001) "*Inflammation in stasis dermatitis upregulates MMP-1, MMP-2 and MMP-13 expression*" *J. Dermatol. Sci.* 25:198-205; Devillers A. C., van Toorenenbergen A. W., Klein Heerenbrink G. J., Muldert P. G. and Oranje A. P. (2007) "*Elevated levels of plasma matrix metalloproteinase-9 in patients with atopic dermatitis: a pilot study*" *Clin. Exp. Dermatol.* 32:311-313; Miyoshi H., Kanekura T., Aoki T. and Kanzaki T. (2005) "*Beneficial effects of tissue inhibitor of metalloproteinases-2 (TIMP-2) on chronic dermatitis*" *J. Dermatol.* 32:346-353]. "Dermatitis" is defined as those skin conditions, disorders or pathologies that cause inflammation, including contact dermatitis, atopic dermatitis, sensitive skin and eczema. It is also known that MMPs are involved in perifollicular matrix degradation, and thus, in hair loss. Specifically, cytokines and the epidermal growth factor stimulate MMP-9 production in the lower epithelial compartment of hair root, such mechanism controls capillary follicle involution observed in alopecia [Jarrousse F., Boisnic S., Branchet M. C., Beranger J. Y., Godeau G., Breton L., Bernard B. A. and Mahé Y. F. (2001) "*Identification of clustered cells in human hair follicle responsible for MMP-9 gelatinolytic activity: consequences for the regulation of hair growth*" *Int. J. Dermatol.* 40:385-392]. Thus, overexpressed MMP inhibition during alopecic processes could be effective in delaying, and even preventing, hair loss [EP 1 076 549 B1].

Also, MMP activity is related to scar formation in tissues containing collagen. "Scar formation is defined as the formation of an abnormal morphological collagen structure due to previous injuries or due to the healing process of tissue containing collagen on the skin.

Healing processes consist of three stages: (1) inflammation, (2) tissue formation and (3) tissue remodeling. A necessary stage in the healing process is extracellular matrix degradation: in order for the cells to proliferate in the wounded area and regenerate it, it is necessary that the extracellular matrix be degraded. Such degradation is made through MMPs. Healing process stages are regulated by a balance between the different MMPs and it has been described that an excess of MMP activity causes chronic ulcers. For example, an overexpression of MMP-8 can be associated to the pathogenesis of leg chronic ulcers. Likewise, diabetic ulcers are characterized by a prolonged inflammation, decrease collagen synthesis and high MMP levels.

Most scars consist of collagen fibers irregularly organized as well as an excess of collagen. Scars have different causes (accidents, surgery, skin diseases, burns, acne, infections and accidents in general), but not all scars are the same. Different kinds of scars can be grouped in Flat and pale scars: formed as a result of the body's natural healing process.

Sunken scars: formed by skin attached to deeper structures, such as muscles, or due to loss of fat in internal tissues. These scars are recessed into the skin and are usually the result of an injury.

Hypertrophic scars: appear when the body produces an excess of collagen during the healing process. These scars elevate over the skin surface and contain irregularly organized collagen.

Keloid scars: formed as a result of an imbalance in the production of collagen during the healing process. These scars not only elevate over skin surface, but also they extend beyond the boundary of the original wound and can continue to grow indefinitely.

Acne scars: formed in skin affected by acne. The scar can be sunken or become a keloid. People who have had chicken pox can have similar scars.

Stretched scars: occur when the skin around a healing wound is put under tension during the healing process. Initially, the scar may appear normal but can widen and thin over a period of weeks or months. This can occur when the wound is close to a joint and is stretched during movement or it may be due to poor healing because of general ill health or malnutrition.

Stretch marks: develop when the skin is stretched rapidly, for example during pregnancy or the adolescent growth spurt.

Therefore, skin scar reduction is desirable both from the pathological point of view, as healing during fibrotic processes, and from the cosmetic point of view, as in the case of softening the aspect of scars caused by acne or stretch marks.

It has also been described that during adipocytes proliferation and differentiation, MMPs are overexpressed [Traurig M. T., Permana P. A., Nair S., Kobes S., Bogardus C. and Baier L. J. (2006) "*Differential expression of matrix metalloproteinase 3 (MMP3) in preadipocytes/stromal vascular cells from nonobese nondiabetic versus obese nondiabetic Pima Indians*" Diabetes 55:3160-3165]. MMP activity inhibition with several specific inhibitors prevents adipocytes differentiation. An especially interesting fact is that MMP inhibitors are able to reduce the accumulation of lipogenic markers (triglycerides) in adipocyte cultures [Demeulemeester D., Collen D. and Lijnen H. R. (2005) "*Effect of matrix metalloproteinase inhibition on adipose tissue development*" Biochem. Biophys. Res. Commun. 329:105-110]. Thus, MMP inhibitors can be developed as anti cellulite agents and help reduce orange peel skin aspect.

MMP activity is also responsible for the extracellular matrix disorganization that surrounds lymphatic and blood vessels. Matrix deterioration around blood vessels allows for a passive vasodilatation which gives place to capillary visibility or telangiectasia, or couperosis. Besides, this microcapillary passive dilatation can cause local blood vessel bursts which can give place to bags under the eyes or dark circles in the periorbital area. Furthermore, MMPs have an influence over vein wall mechanical properties, which can make veins fragile and consequently lead to the development of varicose veins.

Apart from the relation of MMPs to tissue matrix degradation, it has been suggested that MMPs are also involved in different pathologies that concur with an abnormal metabolism of the connective tissue or basal membrane matrix such as arthritis (rheumatoid arthritis, osteoarthritis, etc), bone diseases (osteoporosis, etc.), ectopic angiogenesis, multiple sclerosis, tumors metastasis and tissue ulcers (cornea, stomach, epidermis, etc.) [EP 0 927 161 B1]. Therefore, an MMP inhibitor could be effective in treating and preventing those pathologies caused by an abnormal metabolism of the tissular matrix.

Then, it is widely accepted that MMP activity regulation is highly important for the basal membrane and extracellular matrix protection, as well as for preventing and improving signs of aging. In the context of the present invention, the term "aging" refers to changes experienced by the skin with the passing of years (chrono-aging), or due to sun exposition (photoaging) or due to environmental agents like tobacco smoke, extreme cold or wind weather conditions, chemical pollutants or pollution and it includes all visible external changes as well as those perceptible by touch, such as for example and in a non-limiting sense, development of skin discontinuities such as wrinkles, thin lines, cracks, irregularities or roughness, increase of pore size, loss of elasticity, loss of firmness, loss of smoothness, loss of the capacity to recuperate after deformation, skin hanging such as cheek hanging, appearance of eye pouches or double chin, among others, changes of the skin color, such as marks, reddening, bags under the eyes or the appearance of hyperpigmented areas such as age marks or freckles among others, anomalous differentiation, hyperkeratinization, elastosis, keratosis, orange-peel skin, loss of collagen structuring and other histological changes of the stratum corneum, of the dermis, epidermis, vascular system (for example the appearance of spider veins or telangiectasias) or of those tissues close to the skin, among others.

The cosmetic and pharmaceutical sectors have identified numerous compounds and plant extracts which are effective as MMP inhibitors and there are different bibliographical revisions in literature about MMPs, pathologies associated to their overexpression or their activity increase and the different families of compounds and plant extracts useful to their inhibition. In the state of the art there have been described different approximations to control MPPs activity, including small molecules [Levy D. E., Lapierre E., Liang W, Ye W, Lange C. W, Li X., Grobelny D., Casabonne M., Tyrrell D., Holme K., Nadzan A. and Galardy R. E. (1998) "*Matrix metalloproteinase inhibitors: A structure activity study*" J. Med. Chem. 41:199-223; Wojtowicz-Praga S. M., Dickson R.

B. and Hawkins M. J. (1997) "*Matrix metalloproteinase inhibitors*" *Investigational new Drugs* 15:61-75; Duivenvuurden W. C. M., Hirte H. W. and Singh G. (1997) "*Use of tetracycline as an inhibitor of matrix metalloproteinase activity secreted by human bone metastasizing cancer cells*" *Invasion and Metas.* 17:312-322] peptidic inhibitors [Odake S., Monta Y. and Morikawa T. (1994) "*Inhibition of matrix metalloproteinases by peptidyl hydroxamic acids*" *Biochem. Biophys. Res. Comm.* 199:1442-1446] or antibodies against MMPs [Su J-L., Becherer D., Edwards C., Bukhart W, McMgeehan G. M. and Champion B. R. (1995) "*Monoclonal antibodies against human collagenase and stromelysin*" *Hybridoma* 14:383-390]. Cosmetic industry has made important efforts to offset MMPs activity and the age-related loss of functionality of extracellular matrix components caused by MMPs. Balance between production and degradation of skin essential biomolecules such as collagen evolves with aging towards degradation processes, which leads to, for example, a progressive thinning and disorganization of the dermis which produces dermis flaccidity and a subsequent formation of wrinkles. Therefore, those methods which allow to delay or prevent extracellular matrix degradation will have a potential beneficial effect on mature skins or on aged and/or photo-aged skins; allowing them to partially recover the mechanical properties (elasticity, flexibility and firmness) which they have lost due to age or sun exposure and/or environmental pollutants and thus show a better appearance with fewer wrinkles and a smoother skin. Likewise, MMP inhibition is also an important aspect for the cosmetic sector for applications other than delaying the aging and/or photo-aging, such as for example hair growth modulation [EP 1 076 549 B1] or wound treatments [US 2004/0127420 A1; US 2003/0166567 A1].

Despite the great number of existing compounds and/or extracts, there is still a need to identify new more effective and selective MMP inhibitors.

In the present invention there are described peptides which are effective in MMP inhibition, imitating on this way the function of endogenous MMP inhibitors (TIMP, matrix metalloproteinase tissue inhibitor). The peptide sequence of the invention is not contained in proenzymatic MMP sequences, such as the peptide sequences described in US 2004/0127420 A1 and US 2003/0166567 A1. Sequences similar to the peptides of the invention, without the citrulline residue on the carboxy-terminal (C-terminal), are found in sequences of different enzymes or have enzymatic activity [WO 2004/033668 A2; WO 99/00489 A1]; there is not any clue in the state of the art that suggests the effectiveness of the peptides of the invention as MMP inhibitors, so a person skilled in the art could not deduce the nature of the peptides which inhibit MMPs.

DESCRIPTION OF THE INVENTION

The present invention provides a solution to the above mentioned problem. Surprisingly, the applicant of the present invention has found that certain peptides, whose amino acid sequence does not derive from natural products, are capable of inhibiting MMPs, mainly human MMP-1, MMP-2, MMP-3 and/or MMP-9.

Therefore, peptides in the present invention provide a simple and effective and risk-free solution for the treatment and/or care of skin, mucosae and/or scalp which comprises the application on the skin, mucosae and/or scalp or the oral or parenteral administration of a peptide of general formula (I) to a mammal, as it is described below.

In a first aspect, the invention refers to a peptide according to the general formula (I)

$$R_1\text{-}AA_1\text{-}AA_2\text{-}AA_3\text{-}AA_4\text{-}R_2 \qquad (I)$$

stereoisomers thereof, mixtures thereof or the cosmetically or pharmaceutically acceptable salts thereof, characterized in that:
$AA_1$ is -Arg-;
$AA_2$ is selected from the group consisting of -His- and -Asn-;
$AA_3$ $AA_2$ is selected from the group consisting of -His- and -Arg-;
$AA_4$ is -Cit-;
$R_1$ is selected from the group consisting of H, substituted or non-substituted non-cyclic aliphatic group, substituted or non-substituted alicyclyl, substituted or non-substituted heterocyclyl, substituted or non-substituted heteroarylalkyl, substituted or non-substituted aryl, substituted or non-substituted aralkyl, and $R_5$—CO—; and
$R_2$ is selected from the group consisting of —$NR_3R_4$, —$OR_3$ and —$SR_3$; wherein $R_3$ and $R_4$ are independently selected from the group consisting of H, substituted or non-substituted non-cyclic aliphatic group, substituted or non-substituted alyciclyl, substituted or non-substituted heterocyclyl, substituted or non-substituted heteroarylalkyl, substituted or non-substituted aryl and substituted or non-substituted aralkyl;
wherein $R_5$ is selected from the group consisting of H, substituted or non-substituted non-cyclic aliphatic group, substituted or non-substituted alyciclyl, substituted or non-substituted aryl, substituted or non-substituted aralkyl, substituted or non-substituted heterocyclyl and substituted or non-substituted heteroarylalkyl.

Another aspect of this invention is a process to obtain these peptides of general formula (I).

Another aspect of this invention is aimed at a cosmetic or pharmaceutical composition comprising a cosmetic or pharmaceutical effective amount of at least one peptide of general formula (I), stereoisomers thereof, mixtures thereof or the cosmetically or pharmaceutically acceptable salts thereof, and at least one cosmetically or pharmaceutically acceptable excipient or adjuvant.

In another aspect, the invention is aimed at the use of a peptide of general formula (I), stereoisomers thereof, mixtures thereof or the cosmetically or pharmaceutically acceptable salts thereof, in the preparation of a cosmetic or pharmaceutical composition for the treatment and/or care of skin, mucosae and/or scalp.

DETAILED DESCRIPTION OF THE INVENTION

The peptides of the invention are peptides not derived from natural products; which have an important MMP inhibiting activity and thus, they are useful for the treatment and/or care of those conditions, disorders and/or pathologies of the skin, mucosae and/or scalp resulting from an MMP overexpression or from an increased MMP activity.

Definitions

For a better understanding of the present invention, there are hereby included the meanings of some terms and expressions, as used in the context of the invention.

In the present description, the abbreviations used for amino acids follow the rules of IUPAC-IUB Commission on Biochemical Nomenclature specified in *Eur. J. Biochem.* (1984) 138:9-37 and in *J. Biol. Chem.* (1989) 264:633-673.

So, for example Gly represents NH$_2$—CH$_2$—COOH, Gly- represents NH$_2$—CH$_2$—CO—, -Gly represents —NH—CH$_2$—COOH and -Gly- represents —NH—CH$_2$—CO—. Therefore, the dash representing the peptide bond, eliminates the OH from the 1-carboxyl group of the amino acid (herein represented in the conventional non-ionized form) when it is placed to the right of the symbol, and it eliminates the H from the 2-amino group of the amino acid when it is placed to the left of the symbol; both modifications can be applied to the same symbol (see table 1).

TABLE 1

| Symbol | Residue |
|---|---|
| -Arg- | (structure) |
| -Cit- | (structure) |
| -His- | (structure) |
| -Asn- | (structure) |

In this description, the abbreviation "Ac-" is used to designate the acetyl group (CH$_3$—CO—) and the abbreviation "Palm-" is used to designate palmitoyl group (CH$_3$—(CH$_2$)$_{14}$—CO—).

The term "non-cyclic aliphatic group" is used in the present invention to cover, for example and in a non-limiting sense, linear or branch alkyl, alkenyl and alkynyl groups.

The term "alkyl group" refers to a linear or branched saturated group, which has between 1 and 24, preferably between 1 and 16, more preferably between 1 and 14, even more preferably between 1 and 12, even more preferably 1, 2, 3, 4, 5 or 6 carbon atoms and which is bound to the rest of the molecule by a single bond, including, for example and in a non-limiting sense, methyl, ethyl, isopropyl, isobutyl, terc-butyl, heptyl, octyl, decyl, dodecyl, lauryl, hexadecyl, octadecyl, amyl, 2-ethylhexyl, 2-methylbutyl, 5-methylhexyl and the like.

The term "alkenyl group" refers to a group having between 2 and 24, preferably between 2 and 16, more preferably between 2 and 14, even more preferably between 2 and 12, even more preferably 2, 3, 4, 5 or 6 carbon atoms, with one or more carbon-carbon double bonds, preferably with 1, 2 or 3 conjugated or non-conjugated carbon-carbon double bonds, and which is bound to the rest of the molecule by a single bond, including, for example and in a non-limiting sense, vinyl, oleyl, linoleyl group and the like.

The term "alkynyl group" refers to a group having between 2 and 24, preferably between 2 and 16, more preferably between 2 and 14, even more preferably between 2 and 12, even more preferably 2, 3, 4, 5 or 6 carbon atoms, with one or more conjugated or non-conjugated carbon-carbon triple bonds, preferably with 1, 2 or 3 conjugated or non-conjugated carbon-carbon triple bonds, and which is bound to the rest of the molecule by a single bond, including, for example and in a non-limiting sense, ethynyl, 1-propynyl, 2-propynyl, 1-butynyl, 2-butynyl, 3-butynyl, pentynyl group, such as for example 1-pentynyl and the like.

The term "alicyclic group" is used in the present invention to cover, for example and in a non-limiting sense, cycloalkyl, cycloalkenyl or cycloalkylnyl groups.

The term "cycloalkyl" refers to a saturated mono- or polycyclic aliphatic group which has between 3 and 24, preferably between 3 and 16, more preferably between 3 and 14, even more preferably between 3 and 12, even more preferably 3, 4, 5 or 6 carbon atoms, and which is bound to the rest of the molecule by a single bond, including, for example and in a non-limiting sense, cyclopropyl, cyclobutyl, cyclopentyl, cyclohexyl, cyclohepty, methyl cyclohexyl, dimethyl cyclohexyl, octahydroindene, decahydronaphthalene, dodecahydrophenalene and the like.

The term "cycloalkenyl group" refers to a non-aromatic mono- or polycyclic aliphatic group which has between 5 and 24, preferably between 5 and 16, more preferably between 5 and 14, even more preferably between 5 and 12, even more preferably 5 or 6 carbon atoms, with one or more carbon-carbon double bonds, preferably with 1, 2 or 3 conjugated or non-conjugated carbon-carbon double bonds, and which is bound to the rest of the molecule by a single bond, including, for example and in a non-limiting sense, cyclopent-1-en-1-yl group and the like.

The term "cycloalkynyl group" refers to a non-aromatic mono- or polycyclic aliphatic group which has between 5 and 24, preferably between 5 and 16, more preferably between 5 and 14, even more preferably between 5 and 12, even more preferably 5 or 6 carbon atoms, with one or more carbon-carbon triple bonds, preferably 1, 2 or 3 conjugated or non-conjugated triple bonds carbon-carbon, and which is bound to the rest of the molecule by a single bond, including, for example and in a non-limiting sense, cyclohex-1-yn-1-yl group and the like.

The term "aryl group" refers to an aromatic group which has between 6 and 30, preferably between 6 and 18, more preferably between 6 and 10, even more preferably between 6 or 10 carbon atoms, comprising 1, 2, 3 or 4 aromatic nuclei, bound by a carbon-carbon bond, or fused, including, for example and in a non-limiting sense, phenyl, naphtyl, diphenyl, indenyl, phenanthryl or anthranil among others; or an aralkyl group.

The term "aralkyl group" refers to an alkyl group substituted with an aromatic group, having between 7 and 24 carbon atoms and including, for example and in a non-limiting sense, —$(CH_2)_{1-6}$-phenyl, —$(CH_2)_{1-6}$-(1-naphtyl), —$(CH_2)_{1-5}$-(2-naphtyl), —$(CH_2)_{1-6}$—CH(phenyl)$_2$ and the like.

The term "heterocyclyl group" refers to a 3-10 member hydrocarbon ring, in which one or more of the atoms of the ring, preferably 1, 2 or 3 atoms of the ring, are elements other than carbon, such as nitrogen, oxygen or sulfur and which can be saturated or unsaturated. For the purposes of this invention, the heterocycle can be a monocyclic, bicyclic or tricyclic cyclic system, which can include systems of fused rings; and the nitrogen, oxygen or sulfur atoms can be optionally oxidized in the heterocyclic radical; the nitrogen atom can be optionally quaternized, and the heterocyclyl radical can be partially or completely saturated or be aromatic. The term heterocyclyl more preferably refers to a 5 or 6 member ring.

The term "heteroarylalkyl group" refers to an alkyl group substituted with a substituted or non-substituted aromatic heterocyclyl group, wherein the alkyl group has 1 to 6 carbon atoms and the aromatic heterocyclyl group has between 2 to 24 carbon atoms and from 1 to 3 atoms different from carbon, and including, for example and in a non-limiting sense, —$(CH_2)_{1-6}$-imidazolyl, —$(CH_2)_{1-6}$-triazolyl, —$(CH_2)_{1-6}$-thienyl, —$(CH_2)_{1-6}$-furyl, —$(CH_2)_{1-6}$-pyrrolidinyl and the like.

As it is understood in this technical area, there can be a certain level of substitution on the above defined radicals. Thus, there can be substitution in any of the groups in the present invention. This document references to substituted groups in the groups of the present invention indicate that the specified radical can be substituted in one or more available positions by one or more substituents, preferably in 1, 2 or 3 positions, more preferably in 1 or 2 positions, and even more preferably in 1 position. Said substituents include, for example and in a non-limiting sense, $C_1$-$C_4$ alkyl; hydroxyl; $C_1$-$C_4$ alkoxyl; amino; $C_1$-$C_4$ aminoalkyl; $C_1$-$C_4$ carbonyloxyl; $C_1$-$C_4$ oxycarbonyl; halogen such as fluorine, chlorine, bromine and iodine; cyano; nitro; azido; $C_1$-$C_4$ alkylsulfonyl; thiol; $C_1$-$C_4$ alkylthio; aryloxyl such as phenoxyl; —$NR_b$ (C=$NR_b$)$NR_bR_c$; wherein $R_b$ and $R_0$ are independently selected from the group consisting of H, $C_1$-$C_4$ alkyl, $C_2$-$C_4$ alkenyl, $C_2$-$C_4$ alkynyl, $C_3$-$C_{10}$ cycloalkyl, $C_6$-$C_{18}$ aryl, $C_7$-$C_{17}$ aralkyl, 3-10 member heterocyclyl or protective group of the amino group.

Compounds of the Invention

The compounds of the invention are defined by the general formula (I)

wherein $R_1$, $AA_1$, $AA_2$, $AA_3$, $AA_4$ and $R_2$ have the previously defined meaning.

The $R_1$ and $R_2$ groups are bound to amino-terminal (N-terminal) and carboxy-terminal (C-terminal) ends of the peptide sequence.

According to an embodiment of the present invention, $R_1$ is selected from the group consisting of H or $R_5$—CO—, wherein $R_5$ is selected from the group consisting of the substituted or non-substituted $C_1$-$C_{24}$ alkyl radical, substituted or non-substituted $C_2$-$C_{24}$ alkenyl, substituted or non-substituted $C_2$-$C_{24}$ alkynyl, substituted or non-substituted $C_3$-$C_{24}$ cycloalkyl, substituted or non-substituted $C_5$-$C_{24}$ cycloalkenyl, substituted or non-substituted $C_5$-$C_{24}$ cycloalkynyl, substituted or non-substituted $C_6$-$C_{30}$ aryl, substituted or non-substituted $C_7$-$C_{24}$ aralkyl, substituted or non-substituted 3-10 member heterocyclyl, and substituted or non-substituted heteroarylalkyl with from 2 to 24 carbon atoms and from 1 to 3 atoms different from carbon and an alkyl chain of 1 to 6 carbon atoms. More preferably, $R_1$ is selected from H, acetyl, tert-butanoyl, hexanoyl, 2-methylhexanoyl, cyclohexanecarboxyl, octanoyl, decanoyl, lauroyl, myristoyl, palmitoyl, stearoyl, oleoyl and linoleoyl. Even more preferably, $R_1$ is H, acetyl, lauroyl, myristoyl or palmitoyl. In an even more preferred embodiment, radicals $R_1$ are H, acetyl or palmitoyl.

According to another preferred embodiment, $R_2$ is —$NR_3R_4$, —$OR_3$ or —$SR_3$ wherein $R_3$ and $R_4$ are independently selected from the group consisting of H, substituted or non-substituted $C_1$-$C_{24}$ alkyl, substituted or non-substituted $C_2$-$C_{24}$ alkenyl, substituted or non-substituted $C_2$-$C_{24}$ alkynyl, substituted or non-substituted $C_3$-$C_{24}$ cycloalkyl, substituted or non-substituted $C_5$-$C_{24}$ cycloalkenyl, substituted or non-substituted $C_5$-$C_{24}$ cycloalkynyl, substituted or non-substituted $C_6$-$C_{30}$ aryl, substituted or non-substituted $C_7$-$C_{24}$ aralkyl, substituted or non-substituted 3-10 member heterocyclyl, and substituted or non-substituted heteroarylalkyl with from 2 to 24 carbon atoms and from 1 to 3 atoms different from carbon and an alkyl chain of 1 to 6 carbon atoms. Optionally, $R_3$ and $R_4$ can be bound by a saturated or unsaturated carbon-carbon bond, forming a cycle with the nitrogen atom. More preferably $R_2$ is —$NR_3R_4$ or —$OR_3$, wherein $R_3$ and $R_4$ are independently selected from the group consisting of H, substituted or non-substituted $C_1$-$C_{24}$ alkyl, substituted or non-substituted $C_2$-$C_{24}$ alkenyl, substituted or non-substituted $C_2$-$C_{24}$ alkynyl, substituted or non-substituted $C_3$-$C_{10}$ cycloalkyl, substituted or non-substituted $C_6$-$C_{15}$ aryl and substituted or non-substituted 3-10 member heterocyclyl, and substituted or non-substituted heteroarylalkyl with a 3 to 10 members ring and an alkyl chain of 1 to 6 carbon atoms. More preferably, $R_3$ and $R_4$ are selected from the group consisting of H, methyl, ethyl, hexyl, dodecyl or hexadecyl. More preferably, $R_3$ is H and $R_4$ is selected from the group consisting of H, methyl, ethyl, hexyl, dodecyl or hexadecyl.

According to an even more preferred embodiment, $R_2$ is selected from —OH and —$NH_2$.

Even more preferably, $R_1$ is acetyl and $R_2$ is —OH.

According to an embodiment of the present invention $AA_1$ is -Arg-, $AA_2$ is -His-, $AA_3$ is -His- and $AA_4$ is -Cit-.

According to an embodiment of the present invention, $AA_1$ is -Arg-, $AA_2$ is -Asn-, $AA_3$ is -Arg- and $AA_4$ is -Cit-.

According to another embodiment of the present invention, $R_1$ is selected from the group consisting of H, acetyl, lauroyl, myristoyl or palmitoyl, $AA_1$ is -L-Arg-, $AA_2$ is -L-His-, $AA_3$ is -L-His-, $AA_4$ is -L-Cit- and $R_2$ is —$NR_3R_4$ or —$OR_3$ wherein $R_3$ and $R_4$ are independently selected from the group consisting of H, methyl, ethyl, hexyl, docecyl and hexadecyl groups, preferably $R_2$ is —OH or —$NH_2$. Even more preferably, $R_1$ is acetyl and $R_2$ is —OH.

According to another embodiment of the present invention $R_1$ is selected from the group consisting of H, acetyl, lauroyl, myristoyl or palmitoyl, $AA_1$ is -L-Arg-, $AA_2$ is -L-Asn-, $AA_3$ is -L-Arg-, $AA_4$ is -L-Cit- and $R_2$ is —$NR_3R_4$ or —$OR_3$ wherein $R_3$ and $R_4$ are independently selected from the group consisting of H, methyl, ethyl, hexyl, docecyl and hexadecyl groups, preferably $R_2$ is —OH or —$NH_2$. Even more preferably, $R_1$ is acetyl and $R_2$ is —OH.

In a preferred way, the compounds of formula (I) are selected from the group consisting of:
Ac-Arg-His-His-Cit-OH (Ac-(SEQ ID NO: 1)-OH),
Ac-Arg-Asn-Arg-Cit-OH (Ac-(SEQ ID NO: 2)-OH),
Ac-Arg-Asn-His-Cit-OH (Ac-(SEQ ID NO: 3)-OH),
Ac-Arg-His-Arg-Cit-OH (Ac-(SEQ ID NO: 4)-OH),

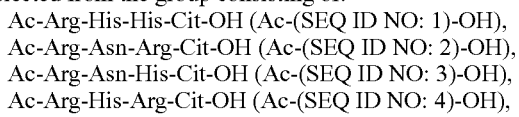

Palm-Arg-His-His-Cit-OH (Palm-(SEQ ID NO: 1)-OH),
Palm-Arg-Asn-Arg-Cit-OH, (Palm-(SEQ ID NO: 2)-OH)
Palm-Arg-Asn-His-Cit-OH, (Palm-(SEQ ID NO: 3)-OH)
Palm-Arg-His-Arg-Cit-OH (Palm-(SEQ ID NO: 4)-OH),
Ac-Arg-His-His-Cit-NH—$(CH_2)_{15}$—$CH_3H_3$) Ac-(SEQ ID NO: 1)-NH—$(CH_2)_{15}$—$CH_3$),
Ac-Arg-Asn-Arg-Cit-NH—$(CH_2)_{15}$—$CH_3$ Ac-(SEQ ID NO: 2)-NH—$(CH_2)_{15}$—$CH_3$),
H-Arg-His-His-Cit-$NH_2$ (H-(SEQ ID NO: 1)-$NH_2$),
and
H-Arg-Asn-Arg-Cit-$NH_2$ (H-(SEQ ID NO: 2)-$NH_2$),
mixtures thereof or cosmetically or pharmaceutically acceptable salts thereof.

The peptides of the present invention can exist as stereoisomers or mixtures of stereoisomers; for example, the amino acids that form them can have a L-, D-configuration or they can be racemic independently from one another. Therefore, it is possible to obtain isomeric mixtures as well as racemic or diastereomeric mixtures or pure diastereoisomers or enantiomers, depending on the number of asymmetric carbons and on which isomers or isomeric mixtures are present. Preferred structures for the peptides of the invention are pure isomers, that is to say, enantiomers or diastereoisomers.

For example when it is stated that $AA_1$ can be -Arg-, it is understood that AA, is selected from -L-Arg-, -D-Arg- or racemic or non-racemic mixtures of both of them. Likewise, when it is said that $AA_2$ can be -His-, it is understood that it can be -L-His-, -D-His- or racemic or non-racemic mixtures of both of them. The methods described in the present document allow the person skilled in the art to obtain each of the stereoisomers of the peptide of the invention by choosing the amino acid with the suitable configuration.

Within the scope of the present invention, there are also included cosmetically or pharmaceutically acceptable salts of peptides provided by this invention. The term "cosmetically or pharmaceutically acceptable salts" means a salt generally recognized for its use in animals, and more particularly in human beings, and it includes the salts used to form base addition salts, either inorganic, such as for example and in a non-limiting sense, lithium, sodium, potassium, calcium, magnesium or aluminium, among others, or organic such as for example and in a non-limiting sense, ethylamine, diethylamine, ethylenediamine, ethanolamine, diethanolamine, arginine, lysine, histidine, or piperazine among others; or acid addition salts, either organic, such as for example and in a non-limiting sense, acetate, citrate, lactate, malonate, maleate, tartrate, fumarate, benzoate, aspartate, glutamate, succinate, oleate, trifluoroacetate, oxalate, pamoate or gluconate among others, or inorganic, such as for example and in a non-limiting sense, chloride, sulfate, borate, or carbonate among others. The nature of the salt is not critical, as long as it is cosmetically or pharmaceutically acceptable. The cosmetically or pharmaceutically acceptable salts of the peptides the invention can be obtained by conventional methods well known in the state of the art [Berge S. M., Bighley L. D. and Monkhouse D. C. (1977) "*Pharmaceutical Salts*" *J. Pharm.* 66:1-19].

Preparation Methods

Invention peptides synthesis, its stereoisomers or its cosmetically or pharmaceutically acceptable salts can be made by means of conventional methods, known in the state of the art, such as by peptide synthesis methods in solid phase [Stewart J. M. and Young J. D. (1984) "*Solid Phase Peptide Synthesis, 2nd edition*" Pierce Chemical Company, Rockford, Ill.; Bodanzsky M. and Bodanzsky A. (1984) "*The practice of Peptide Synthesis*" Springer Verlag, New Cork; Lloyd-Williams P., Albericio F. and Giralt E. (1997) "*Chemical Approaches to the Synthesis of Peptides and Proteins*" CRC, Boca Raton, Fla., USA], solution synthesis, a combination synthesis in solid phase methods and in solution or enzymatic synthesis [Kullmann W. (1980) "*Proteases as catalysts for enzymic syntheses of opioid peptides*" *J. Biol. Chem.* 255: 8234-8238]. Peptides can also be obtained by bacterial strain fermentation modified or not, by genetic engineering so as to obtain the desired sequences or by animal or vegetal protein controlled hydrolysis, preferably vegetal, releasing peptide fragments containing at least the desired sequence.

For example, a method for obtaining the peptides of the invention having the (I) formula, includes the following stages:

amino acid coupling, having the N-terminal end protected and C-terminal free, on an amino acid with its N-terminal end free and the C-terminal end protected or joined to a solid support;

protecting group elimination from the N-terminal end;

coupling sequence repetition and N-terminal end elimination until the desired peptide sequence is obtained;

protecting group elimination from the C-terminal end or solid support excision.

Preferably, C-terminal end is joined to a solid support and the process takes place in solid phase, thus, it comprises the amino acid coupling with the N-terminal protected end and the C-terminal free end on an amino acid with its N-terminal free and the C-terminal joined to a polymeric support; protecting group elimination from the N-terminal end; and repetition of this sequence as many times as needed until a tetrapeptide is obtained, and finally the original polymeric support synthesized peptide is removed through excision.

Functional groups in amino acid side chains are conveniently protected by temporal or permanent protecting groups throughout the synthesis, and can simultaneously or orthogonally be unprotected to the polymeric support peptide excision.

Alternatively, solid phase synthesis can take place via a convergent strategy coupling a dipeptide or a tripeptide over the polymeric support or on a dipedtide or amino acid previously joined to the polymeric support. Convergent synthesis strategies are widely known by subject experts and are described in Lloyd-Williams P., Albericio F. and Giralt E. en "*Convergent solid-phase peptide synthesis*" (1993) *Tetrahedron* 49:11065-11133.

The process can comprise additional stages such as N-terminal and C-terminal unprotection and/or random order polymeric support peptide excision, using standard processes and conditions known in the field, after which the functional groups of said ends can be modified. Optional N-terminal and C-terminal ends modification can be done with a formula (I) peptide anchored to the polymeric support or once the peptide has been removed from the polymeric support.

Optionally, $R_1$ can be introduced through the N-terminal end reaction of the peptide of the invention with a $R_1$—X wherein $R_1$ has the above mentioned meaning and X is a salient group, such as for example and in a non-limiting sense, tosyl group, mesyl group and halogen groups among others, by a nucleophilic substitution reaction, in presence of the right bases and solvents and wherein such fragments have those functional groups which do not participate in N—C bond formation, conveniently protected by temporal or permanent protected groups.

Optionally and/or additionally, $R_2$ radicals can be introduced by a $HR_2$ compound reaction wherein $R_2$ is —$OR_3$, —$NR_3R_4$ or —$SR_3$, with a complementary fragment corresponding to the formula (I) peptide wherein $R_2$ is —OH in the presence of the right solvent and base such as for example, N,N diisopropylethylamine or triethylamine or an additive such as 1-hydroxybenzotriazole (HOBt) or hydroxybenzotriazole (HOAt) and a dehydrant agent such as, carbodiimide, an uranium salt, a phosphonium salt or an amidinium salt, among others or by previously forming an acyl halide with, for example, thionyl chloride, so as to obtain a peptide of general formula (I) according to the invention, wherein such fragments present those functional groups that do not participate in N—C bond formation, conveniently protected by temporal or permanent protected groups or alternatively, other $R_2$ radicals can be introduced by simultaneous incorporation to the process of polymeric support peptide excision.

A subject expert will easily understand that C-terminal and N-terminal ends unprotection/excision stages and its later derivatization can take place in any order, according to processes known in the field [Smith, M. B. and March, J. (1999) "*March's Advanced Organic Chemistry Reactions, Mechanisms and Structure*", 5th Edition, John Wiley & Sons, 2001].

The term "protecting group" refers to a group which blocks an organic functional group and can be eliminated under controlled conditions. Protecting groups, their relative reactivities and the conditions under which they stay inert are known by the subject expert.

Examples of representative protecting groups for the amino group are amides such as, amide acetate, benzoate amide, pivalate amide; carbamates such as, bencyloxycarbonyl (Cbz), para-nitrobenzyloxycarbonyl (pNZ), terc-butyloxycarbonyl (Boc), 2,2,2-trichloroethoxycarbonyl (Troc), 2-(trimethylsilyl)ethoxycarbonyl (Teoc), 9-fluorenylmethyloxicarbonyl (Fmoc), alyloxycarbonyl (Alloc), among others; preferably, Boc or Fmoc.

Examples of representative groups for the carboxyl group are esters such as, terc-butyl ester (tBu), allyl ester (All), triphenylmethyl ester (trityl ester, Trt), cyclohexyl ester (cHex), benzyl ester (Bzl), o-nitrobenzyl ester, p-nitrobenzyl ester, p-methoxybenzyl ester, trimethylsilyl ester, among others; invention preferred protecting groups are All, tBu, cHex, Bzl and Trt esters.

Trifunctional amino acids can be protected during synthetic process with temporal or permanent orthogonal protecting groups to N-terminal and C-terminal end protecting groups. Arginine guinidine group can be protected with 2,2,5,7,8-pentamethylcroman-6-sulfonyl (Pmc) group, 2,2,4,6,7-pentamethyldihydrobenzofuran-5-sulfonil (Pbf), para-toluenesulfonyl (tosyl, Tos) or 4-metoxi-2,3,6-trimethylbenzenesulfonyl (Mtr), among others; the histidine imidazole group can be protected with tosyl group (Tos), terc-butyloxycarbonyl group (Boc), trityl group (Trt), methyltrityl group (Mtt) or the 2,4-dinitrophenyl group (Dnp) among others; and the asparagine amide group can be protected with trityl group (Trt) or the xanthyl group (Xan) or being used without protection from the amide group.

In a preferred embodiment, the group protection strategy used is the strategy in which amino groups are protected through Boc, carboxyl groups are protected through Bzl, cHex or All, the arginine side chain is protected with Mtr or Tos, the asparagine chain is used without protection and the histidine chain is protected with Tos or Dnp.

In another preferred embodiment, the group protection strategy used is the strategy in which amino groups are protected through Fmoc, carboxyl groups are protected with tBu, All or Trt, the arginine side chain is protected with Pmc or Pbf, the asparagine chain is protected with Trt and histidine chain with Trt or Mtt.

Examples of these and other additional protecting groups, its introduction and elimination can be found described in [Greene T. W. and Wuts P. G. M., (1999) "*Protective groups in organic synthesis*" John Wiley & Sons, New York; Atherton B. and Sheppard R. C. (1989) "*Solid Phase Peptide Synthesis: A practical approach*" IRL Oxford University Press]. The term "protecting groups" includes also polymeric supports employed in solid phase synthesis.

When the synthesis is totally or partially done in solid phase, some of the solid supports to be used in the invention method, are polystyrene supports, polyethylenglycol engrafted in polystyrene and similar ones, such as for example and in a non-limiting sense, p-methylbenzhydrylamine resins (MBNA) [Matsueda G. R. and Stewart J. M. (1981) "*A p-methylbenzhydrylamine resin for improved solid-phase synthesis of peptide amides*" Peptides 2:45-50], 2-chlorotrityl resins [Barlos K., Gatos D., Kallitsis J., Papaphotiu G., Sotiriu P., Wenqing Y. and Schäfer W. (1989) "*Darstellung geschützter Peptid-fragmente unter Einsatz substituierter Triphenylmethyl-harze*" Tetrahedron Lett. 30:3943-3946; Barlos K., Gatos D., Kapolos S., Papaphotiu G., Schäfer W. and Wenqing Y. (1989) "*Veresterung von partiell geschützten Peptid-fragmenten mit Harzen. Einsatz von 2-Chlorotritylchlorid zur Synthese von Leu15-gastrin I*" Tetrahedron Lett. 30:3947-3951], TentaGel® resins (Rapp Polymere GmbH), Chem Matrix® resins (Matrix Innovation, Inc) and similar ones, which may or may not include a labile spacer such as, 5-(4-aminomethyl-3,5-dimethoxy-phenoxy) valeric acid (PAL) [Albericio F., Kneib-Cordonier N., Biancalana S., Gera L., Masada R. I., Hudson D. and Barany G. (1990) "*Preparation and application of the 5-(4-(9-fluorenylmethyloxycarbonyl)aminomethyl-3,5-dimethoxy-phenoxy)-valeric acid (PAL) handle for the solid-phase synthesis of C-terminal peptide amides under mild conditions*" J. Org. Chem. 55:3730-3743] the 2-[4-aminomethyl-(2,4-dimethoxyphenyl)] phenoxyacetic acid (AM) [Rink H. (1987) "*Solid-phase synthesis of protected peptide fragments using a tri-alkoxy-diphenyl-methylester resin*" Tetrahedron Lett. 28:3787-3790], Wang [Wang S. S. (1973) "*p-Alkoxybenzyl Alcohol Resin and p-Alkoxybenzyloxycarbonylhydrazide Resin for Solid Phase Synthesis of Protected Peptide Fragments*" J. Am. Chem. Soc. 95:1328-1333] and similar ones which enable simultaneous unprotection and excision of the polymeric support peptide.

Cosmetic or Pharmaceutical Compositions

The peptides of the invention can be administered to inhibit MMPs by any means making contact of the peptides with the site of action thereof in the body of a mammal, preferably human beings, and in the form of a composition containing them.

In this sense, another aspect of the invention is a cosmetic or pharmaceutical composition comprising at least one peptide of general formula (I), stereoisomers thereof, mixtures thereof or its cosmetically or pharmaceutically acceptable salts with at least one cosmetically or pharmaceutically acceptable adjuvant. These compositions can be prepared by conventional methods, known persons skilled in the art ["*Harry's Cosmeticology*", Eight edition (2000) Rieger M. M., ed., New York Chemical Pub., NY, US; "*Remington: The Science and Practice of Pharmacy*", Twentieth edition (2003) Genaro A. R., ed., Lippincott Williams & Wilkins, Philadelphia, US].

The peptides of the present invention have a variable water-solubility, according to the nature of their sequence or the possible modifications they have at the N-terminal and/or C-terminal ends. Therefore, the peptides of the present invention can be incorporated into the compositions by means of aqueous solution, and those which are not water-soluble can be solubilized in conventional cosmetically or pharmaceutically acceptable solvents, such as for example and in a non-limiting sense, ethanol, propanol, isopropanol, propylene glycol, glycerin, butylene glycol or polyethylene glycol or any combination thereof.

The cosmetically or pharmaceutically effective amount of the peptides of the invention to be administered to treat a condition, disorder and/or pathology, as well as their dosage, will depend on diverse factors, including the age, condition of the patient, the severity of the disorder or pathology, the route and frequency of administration and on the particular nature of the peptides to be used.

"Cosmetically or pharmaceutically effective amount" means a non-toxic amount of peptide(s) which is enough to provide the desired effect. Peptides of the invention are used in the cosmetic or pharmaceutical composition of the present invention at concentrations than are cosmetically or pharmaceutically effective to obtain the desired effect; preferably, regarding to the total weight of the composition, between 0.00000001% (by weight) and 20% (by weight); preferably between 0.000001% (by weight) and 20% (by weight), more preferably between 0.0001% (by weight) and 10% (by weight) and even more preferably between 0.0001% (by weight) and 5% (by weight).

The peptides of the invention can also be incorporated into cosmetic or pharmaceutical delivery systems and/or sustained release systems.

The term "delivery systems" refers to a diluent, adjuvant, excipient or carrier with which the peptide of the invention is administered. Such cosmetic or pharmaceutical carriers can be liquids; such as water, oils or surfactants, including the ones with petroliferous, animal, plant or synthetic origin; such as for example and in a non-limiting sense peanut oil, soybean oil, mineral oil, sesame oil, castor oils, polysorbates, sorbitan esters, ether sulfate, sulfates, betaines, glucosides, maltosides, fatty alcohols, nonoxynols, poloxamers, polyoxyethylenes, polyethylene glycols, dextrose, glycerol, digitonin and the like.

In "*Remington's Pharmaceutical Sciences*" by E. W. Martin, there are solvents, adjuvants or excipients described as suitable carriers.

The term "sustained release" is used in a conventional sense referring to a delivery system for a compound providing the gradual release of said compound during a period of time and preferably, although not necessarily, with constant levels of compound release throughout a period of time.

Examples of delivery systems or sustained release systems are liposomes, mixed liposomes, milliparticles, microparticles, nanoparticles, solid lipidic nanoparticles, sponges, cyclodextrins, vesicles, micelles, surfactant mixed micelles, phospholipid-surfactant mixed micelles, millispheres, microspheres, nanospheres, liposomes, millicapsules, microcapsules, nanocapsules, as well as microemulsions and nanoemulsions, which can be added in order to obtain a greater penetration of the active ingredient and/or to improve its pharmacokinetic and pharmacodynamic properties.

The sustained release formulations can be prepared by means of methods known in the state of the art, and the compositions containing them can be administered, for example, by topical administration, including the adhesive patches and non-adhesive patches and microelectric patches, or by systemic administration, such as for example and in a non-limiting sense, by oral, nasal, rectal route, subcutaneous implantation or injection, or direct implantation or injection in a specific part of the body, and, preferably, they have to release a relatively constant amount of the peptides of the invention. The amount of peptide contained in the sustained release formulation will depend, for example, on the site of administration, the kinetics and the duration of the release of the peptide of the invention, as well as the nature of the condition, disorder and/or pathology to be treated or prevented.

The peptides of the present invention can also be absorbed on solid organic polymers or solid mineral supports, such as for example and in a non-limiting sense, talcum powder, bentonite, silica, starch and maltodextrin among others.

The peptides of the invention can also be incorporated into fabrics, non-woven fabrics or medical devices which are in direct contact with the skin, mucosae and/or the scalp, so that they release the peptides of the invention either by biodegradation of the anchorage system to the fabric, non-woven fabric or medical devices or by the friction of the latter with the body, by body moisture, by pH of the skin or by body temperature. Likewise, the fabrics and non-woven fabrics can be used to make garments which are in direct contact with the body. Preferably, the fabrics, non-woven fabrics and medical devices containing the peptides of the invention are used for the treatment and/or care of those conditions, disorders and/or pathologies of the skin, mucosae and/or the scalp, which result from MMP overexpression or an increase in the MMP activity.

Examples of fabrics, non-woven fabrics, garments, medical devices and means for immobilizing the peptides to them, including the delivery systems and/or sustained release systems described above, are described in the literature and are known in the state of the art [Schaab C. K. (1986) "*Impregnating Fabrics With Microcapsules*", *HAPPI* May 1986; Nelson G. (2002) "*Application of microencapsulation in textiles*" *Int. J. Pharm.* 242:55-62; "*Biofunctional Textiles and the Skin*" (2006) *Curr. Probl. Dermatol.* v.33, Hipler U. C. and Elsner P., eds. S. Karger A G, Basel, Switzerland; Malcom R. K., McCullagh S. D., Woolfson A. D., Gorman S. P., Jones D. S. and Cuddy J. (2004) "*Controlled release of a model antibacterial drug from a novel self-lubricating silicone biomaterial*" *J. Cont. Release* 97:313-320]. Preferred fabrics, non-woven fabrics, garments, medical devices are bandages, gauzes, T-shirts, socks, pantyhose, underwear, girdles, gloves, diapers, sanitary napkins, dressings, bedcovers, wipes, hydrogels, adhesive patches, non-adhesive patches, microelectric patches and/or face masks.

Cosmetic or pharmaceutical preparations containing the peptides of the present invention, stereoisomers thereof, mixtures thereof or the cosmetically or pharmaceutically acceptable salts thereof, can be used in different types of formulations of topical or transdermal application which will include, optionally, the cosmetically or pharmaceutically acceptable excipients necessary for the formulation of the desired dosage form [Fauli i Trillo C. (1993) in "*Tratado de Farmacia Galénica*", Luzán 5, S. A. Ediciones, Madrid].

The topical or transdermal application formulations can be presented in any solid, liquid or semi-solid dosage form, such as for example and in a non-limiting sense, creams, multiple emulsions such as for example and in a non-limiting sense emulsions of oil and/or silicone in water, emulsions of water in oil and/or silicone, emulsions of the water/oil/water or water/silicone/water type and emulsion of the oil/water/oil or silicon/water/silicon type, anhydrous compositions, aqueous dispersions, oils, milks, balsams, foams, lotions, gels, cream gels, hydroalcoholic solutions, hydroglycolic solutions, liniments, saline solutions, soaps, shampoos, conditioners, sera, polysaccharide films, unguents, mousses, ointments, powders, bars, pencils and aerosols or sprays, including leave-on formulations and rinse-off formulations. These topical or transdermal application formulations can be incorporated by techniques known by the person skilled in the art to different types of solid accessories, such as for example and in a non-limiting sense, wipes, hydrogels, adhesive patches, non-adhesive patches, microelectric patches or face masks; or they can be incorporated to different makeup line products such as makeup foundations; such as for example fluid or solid makeup foundations, makeup removal lotions, makeup removal milks, under eye concealers, eye shadows, lipsticks, lip protectors, lip glosses and powders, among others.

The cosmetic or pharmaceutical compositions of the invention can include agents which increase the percutaneous absorption of the peptides of the present invention, such as for example and in a non-limiting sense, dimethylsulfoxide, dimethylacetamide, dimethylformamide, surfactants, azone (1-dodecylazacycloheptan-2-one), alcohol, urea, ethoxydiglycol, acetone, propylene glycol or polyethylene glycol among others. Likewise, the cosmetic or pharmaceutical compositions object of the present invention can be applied to local areas to be treated by iontophoresis, sonophoresis, electroporation, microelectric patches, mechanic pressure, osmotic pressure gradient, occlusive treatment, microinjections, or pressure needle-free injections by means of pressure, such as for example, oxygen pressure injections, or any combination thereof, for the purpose of achieving greater penetration of the peptide of the invention. The application area will be determined by the nature of the condition, disorder and/or pathology to be prevented or treated.

Likewise, the cosmetic compositions containing the peptides of the present invention, stereoisomers thereof, mixtures thereof or the cosmetically or pharmaceutically acceptable salts thereof can be used in different kinds of formulations for their oral administration, preferably in the form of oral cosmetics, such as for example and in a non-limiting sense, capsules, including gelatin capsules, tablets, including sugar coated tablets, powders, granulated forms, chewing gums, solutions, suspensions, emulsions, syrups, polysaccharides films, jellies or gelatins as well as any other presentation known by a person skilled in the art. Particularly, the peptides of the invention can be incorporated into any form of functional or fortified food such as for example and in a non-limiting sense, diet bars or compact or non-compact powders. Such powders can be solubilized in water, soda, dairy products, soy derivatives, or they can be incorporated into diet bars. The peptides of the present invention can be formulated with excipients and adjuvants usual for oral compositions or food supplements such as for example and in a non-limiting sense, fat components, aqueous components, humectants, preservatives, texturizing agents, flavors, aromas, antioxidants and colorants commonly found in the food industry.

Cosmetic or pharmaceutical compositions containing the peptides of the present invention, stereoisomers thereof, mixtures thereof or the cosmetically or pharmaceutically acceptable salts thereof can be administered, not only by transdermal or topical routes, but also by any other type of suitable route, for example by oral or parenteral route, for which they will include the pharmaceutically acceptable excipients necessary for the formulation of the desired dosage form. In the context of the present invention, the term "parenteral" includes nasal route; rectal route; subcutaneous, intradermal or intravascular injections; such as intravenous, intramuscular, intravitreal, spinal, intracranial, intraarticular, intrathecal, and intraperitoneal injections; as well as any other similar injection or infusion technique, A revision of the different pharmaceutical dosage form of active ingredients and of the necessary excipients for obtaining said dosage form can be found in "*Tratado de Farmacia Galénica*", C. Fauli i Trillo, 1993, *Luzán* 5, S. A. Ediciones, Madrid.

Among the cosmetically or pharmaceutically acceptable adjuvants described in the present invention, there are included additional ingredients commonly used in compositions for the treatment and/or care of skin, mucosae and/or scalp such as for example and in a non-limiting sense, other agents inhibiting MMP, agents stimulating or inhibiting melanin synthesis, whitening or depigmenting agents, propigmenting agents, self-tanning agents, anti-age agents, NO-synthase inhibiting agents, antioxidant agents, free radicals scavengers and/or anti-atmospheric pollution agents, anti-glycation agents, emulsifying agent, emollients, organic solvents, liquid propellants, skin conditioners such as humectants, substances retaining moisture, alphahydroxyacids, betahydroxyacids, moisturizers, epidermic hydrolytic enzymes, vitamins, pigments or colorants, dyes, gelling polymers, thickeners, surfactants, softeners, anti-wrinkle agents, agents capable of reducing or treating bags under the eyes, exfoliating agents, antimicrobial agents, fungicide agents, fungistatic agents, bactericide agents, bacteriostatic agents, agents stimulating the synthesis of dermal or epidermal macromolecules and/or agents capable of preventing or inhibiting their degradation, agents stimulating collagen synthesis, agents stimulating elastin synthesis, agents stimulating decorine synthesis, agents stimulating laminin synthesis, agents stimulating defensin synthesis, agents stimulating chaperone synthesis, agents stimulating aquaporin synthesis, agents stimulating hyaluronic acid synthesis, agents stimulating the synthesis of lipids and components of the stratum corneum (ceramides, fatty acids, etc.), other agents inhibiting collagen degradation, agents inhibiting elastin degradation, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents inhibiting acetylcholinesterase, dermorelaxing agents, agents stimulating glycosaminoglycan synthesis, DNA repairing agents, DNA protecting agents, anti-itching agents, agents for the treatment and/or care of sensitive skin, firming agents, anti-stretch mark agents, astringent agents, agents regulating sebum production, agents stimulating lipolysis, anticellulitic agents, agents stimulating healing, coadjutant healing agents, agents stimulating reepithelizing, coadjutant reepithelizing agents, cytokine growth factors, calming agents, anti-inflammatory agents, agents acting on capillary circulation and/or microcirculation, agents stimulating angiogenesis, agents inhibiting vascular permeability, agents acting on cell metabolism, agents intended to improve the dermal-epidermal junction, agents inducing hair growth, agents inhibiting or delaying hair growth, preservatives, perfumes, chelating agent, plant extracts, essential oils, marine extracts, agents coming from a bio-fermentation process, mineral salts, cell extracts and sunscreens (organic or mineral photoprotecting agents that are active against ultraviolet A and/or B rays), among others, as long as they are physically and chemically compatible with the remaining components of the composition and specially with the peptides of general formula (I) contained in the composition of the present invention. Likewise, the nature of these additional ingredients should not unacceptably alter the benefits of the peptides of the present invention. Said additional ingredients can be synthetic or natural such as for example plant extracts, or come from a bio-fermentation process. Additional examples can be found in *CTFA Cosmetic Ingredient Handbook, Eleventh Edition* (2006).

An additional aspect of the present invention refers to a cosmetic or pharmaceutical composition containing a cosmetically or pharmaceutically effective amount of at least one peptide of the invention, stereoisomers thereof, mixtures thereof or the cosmetically or pharmaceutically acceptable salts thereof and also a cosmetically or pharmaceutically effective amount of at least one synthetic component, natural extract or product from biofermentation process with activity inhibiting MMP such as for example and in a non-limiting sense, natural extracts containing ursolic acid, isoflavones like genistein, quercetin, carotenoid, lycophene, soybean extract, blueberry extract, rosemary extract, *Trifolium pratense* (red clover) extract, *Phormium tenax* (formio) extract, kakkon-to extract, *salvia* extract, retinol and its derivatives, retinoic acid and its derivatives, sapogenins such as for example and in a non-limiting sense, diosgenin, hecogenin, smilagenin, sarsapogenin, tigogenin, yamogenin and yucagenin among others, Collalift® [INCI: Hydrolyzed Malt Extract], Juvenesce [INCI: Ethoxydiglicol and Caprylic Triglyceride, Retinol, Ursolic Acid, Phytonadione, Ilomastat] or EquiStat [INCI *Pyrus Malus* Fruit Extract, *Glycine Soja* Seed Extract] marketed by Coletica/Engelhard, Pepha®-Timp [INCI: Human Oligopeptide-20], Regu-Age [INCI: Hydrolyzed Rice Bran Protein, *Glycine Soja* Protein, Oxido Reductases] or Colhibin [INCI: Hydrolyzed Rice Protein] marketed by Pentapharm, Lipeptide [INCI: Hydrolyzed vegetable protein] marketed by Lipotec, Litchiderm™ [INCI: Litchi Chinensis pericarp extract] or Arganyl™ [INCI: Argania Spinosa Leaf Extract] marketed by Laboratories Sérobiologiques/Cognis, MDI Complex® [INCI: glycosaminoglycans] or ECM-Protect® [INCI: Water (Aqua), Dextran, Tripeptide-2] marketed by Atrium Innovations, Dakaline [INCI: *Prunus amygdalus dulcis, Anogeissus leiocarpus* bark extract] marketed by Soliance, Homeostatine [INCI: *Enteromorpha compressa, Caesalpinia Spinosa*] marketed by Provital, Timp-Peptide [proposed INCI: Acetyl Hexapeptide] or ECM Moduline [proposed INCI: Palmitoyltripeptide] marketed by Infinitec Activos, IP2000 [INCI: Dextran, Trifluoroacetyl tripeptide-2] marketed by Institut Europeen de Biologie Cellulaire, Actimp 1.9.3® [INCI: Hydrolyzed Lupine Protein] marketed by Expanscience Laboratories, Vitaderm® [INCI: Alcohol, Water (Aqua), Glycerin, Hydrolyzed Rice Protein, Ilex Aquifolium Extract, Sodium Ursolate, Sodium Oleanolate] marketed by Rahn, adapalene, tetracycline and its derivatives such as, minocycline, rolitetracycline, chlortetracycline, metacycline, oxytetracycline, doxycycline, demeclocycline and its salts, Batimastat [BB94; [4-(N-hydroxyamine)-2R-isobutyl-3S-(thiophen-2-ylthiomethyl) succinyl]-L-phenylalanine-N-methylamide], Marimastat [BB2516; [2S—[N4(R*),2R*,3S]]—N4[2,2-dimethyl-1-[methylaminocarbonyl]propyl]-N1,2-dihydroxy-3-(2-methylpropyl)butanediamine], among others.

Likewise, the cosmetic or pharmaceutical compositions of the present invention can additionally contain a cosmetically or pharmaceutically effective amount of at least one analgesic and/or anti-inflammatory compound aiming at reducing swelling and irritation associated to inflammatory processes wherein there is MMP overexpression and/or overactivity. Among these compounds we can highlight synthetic compounds such as hydrocortisone, clobetasol, dexamethasone, prednisone, paracetamol, acetylsalicylic acid, amoxiprin, benorilate, choline salicylate, diflunisal, faislamine, methyl salicylate, magnesium salicylate, salsalate, diclofenac, aceclofenac, acemetacin, bromfenac, etodolac, indomethacin, sulindac, tolmetin, ibuprofen, carprofen, fenbufen, fenoprofen, flurbiprofen, ketoprofen, ketorolac, loxoprofen, naproxen, oxaprozine, tiaprofenic acid, suprofen, mefenamic acid, meclofenamate, meclofenamic acid, tolfenamic acid, nabumetone, phenylbutazone, azapropazone, metamizole, oxyphenbutazone, sulfinpyrazone, piroxicam, lornoxicam, meloxicam, tenoxicam, celecoxib, etoricoxib, lumiracoxib, parecoxib, rofecoxib, valdecoxib, nimesulide, licofelone, omega-3 fatty acid and its biometabolites, morphine, codeine, oxycodone, hydrocodone, diamorphine, pethidine, tramadol, brupenorphine, benzocaine, lidocaine, chloroprocaine, tetracaine, procaine, tricyclic antidepressants, amitriptyline, carbamazepine, gabapentin, pregabalin, sabolol, panthenol, biotin, tocopheryl lauriminodipropionate phosphate, disodium, ciclopirox olamine, nordihydroguaiaretic acid, Neutrazen™ [INCI: Water (Aqua), Butylenen Glycol, Dextran, Palmitoyl Tetrapeptide-8] marketed by Atrium Innovations, Meliprene® [INCI: Dextran, Acetyl Heptapeptide-1] marketed by Institut Europeen de Biologie Cellulaire, coenzyme Q10 or alkylglycerol ethers, or natural extracts or essential oils with analgesic and/or anti-inflammatory activity such as for example and in a non-limiting sense, madecassoside, echinacine, amaranth seed oil, sandalwood oil, placenta extract, peach tree leaf extract, *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca alternifolia, Origanum majorana, Salix alba, Silybum marianum, Tanacetum parthenium* or *Uncaria guianensis*, among others.

Additionally, the present invention refers to a cosmetic or pharmaceutical composition comprising a cosmetically or pharmaceutically effective amount of at least one peptide of general formula (I), stereoisomers thereof, mixtures thereof or the cosmetically or pharmaceutically acceptable salts thereof and also a cosmetically or pharmaceutically effective amount of at least one extract or extract combination with healing and/or reepithelizing activity or effective as coadjuvants in healing and/or reepithelizing processes such as extracts of *Centella asiatica, Rosa moschata, Echinacea angustifolia, Symphytum officinal, Equisetum arvense, Hypericum perforatum, Mimosa tenuiflora, Aloe vera*, Polyplant® Epithelizing [INCI: *Calendula Officinalis, Hypericum Perforatum, Chamomilla Recutita, Rosmarinus Officinalis*] marketed by Provital, Cytokinol® LS 9028 [INCI: Hydrolyzed Casein, Hydrolyzed Yeast Protein, Lysine HCl] marketed by Laboratories Sérobiologiques/Cognis or Deliner® [INCI: *Zea May* (Corn) Kernel Extract] marketed by Coletica/Engelhard among others, and/or a cosmetically or pharmaceutically effective amount of at least one synthetic compound, extract or product coming from a biofermetation process with healing and/or reepithelizing activity or effective as coadjuvants in healing and/or reepithelizing processes such as for example and in a non-limiting sense, cadherins, integrins, selectins, hyaluronic acid receptors, immunoglobulins, fibroblast growth factors, connective tissue growth factor, platelet growth factor, endothelial vascular growth factor, epidermal growth factor, insulin-like growth factor, keratinocyte growth factor, colony-stimulating factors, transforming growth factor-beta, tumor necrosis factor-alpha, interferons, interleukins, matrix metalloproteases, protein tyrosine phosphatase receptors, Antarcticine® [INCI: *Pseudoalteromonas* Ferment Extract] or Decorinyl™ [INCI: Tripeptide-10 Citrulline], marketed by Lipotec, among others.

An additional aspect of the present invention refers to a cosmetic or pharmaceutical composition comprising a cosmetically or pharmaceutically effective amount of at least one peptide of general formula (I), stereoisomers thereof, mixtures thereof or the cosmetically or pharmaceutically acceptable salts thereof and also a cosmetically or pharmaceutically effective amount of at least one extract with anti-wrinkle and/or antiaging activity such as for example and in a non-limiting sense, extracts of *Vitis vinifera, Rosa caning, Curcuma longs, Iris pallida, Theobroma cacao, Ginkgo biloba,* or *Dunaliella salina*, among others, and/or at least one synthetic compound, extract or product coming from a biofermetation process with anti-wrinkle and/or antiaging activity such as for example and in a non-limiting sense, Matrixyl® [INCI: Palmitoyl Pentapeptide-3] or Matrixyl 3000® [INCI: Palmitoyl Tetrapeptide-3, Palmitoyl Oligopeptide] marketed by Sederma, Vialox® [INCI: Pentapeptide-3] or Syn-ake® [INCI: Dipeptide Diaminobutyroyl Benzylamide Diacetate] marketed by Pentapharm, Myoxinol™ [INCI: Hydrolyzed *Hibiscus Esculentus* Extract] marketed by Laboratoires Sérobiologiques/Cognis, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8] (Acetyl hexapeptide-8), Leuphasyl® [INCI: Pentapeptide-18] (Pentapéptido-18), Aldenine® [INCI: Hydrolized wheat protein, hydrolized soy protein, tripeptide-1], Trylagen™ [INCI: *Pseudoalteromonas* Ferment Extract, Hydrolyzed Wheat Protein, Hydrolyzed Soy Protein, Tripeptide-10 Citrulline, Tripeptide-1]; Eyeseryl® [INCI: Acetyl Tetrapeptide-5] or Lipochroman-6 [INCI: Dimethylmethoxy Chromanol] marketed by Lipotec, Kollaren® [INCI: Tripeptide-1, Dextran] marketed by Institut Europeen de Biologie Cellulaire, Collaxyl® [INCI: Hexapeptide-9] or Quintescine® [INCI: Water, Butylene Glycol, Dipeptide-4] marketed by Vincience, BONT-L-Peptide [proposed INCI: Palmitoyl Hexapeptide] marketed by Infinitec Activos, $Ca^{2+}$ channel antagonists such as alverine, manganese or magnesium salts, certain secondary or tertiary amines, retinol and its derivatives, idebenone and its derivatives, coenzyme Q10 and derivatives, boswellic acid and its derivatives or agonist of chloride channel, among others.

An additional aspect of present invention refers to a cosmetic or pharmaceutical composition comprising a cosmetically or pharmaceutically effective amount of at least one peptide of general formula (I), and also a cosmetically or pharmaceutically effective amount of at least one extract or combination of extracts with refirming, rethickening and/or restructuring activity, such as for example and in a non-limiting sense, *Malpighia punicitolia, Cynara scolymus, Gossypium herbaceum, Aloe Barbadensis, Panicum miliaceum, Morus nigra, Sesamum indicum, Glycine soy, Triticum vulgare*, Pronalen® Refirming HSC [INCI: *Triticum vulgare, Silybum Marianum, Glycine Soy, Equisetum Arvense, Alchemilla Vulgaris, Medicago Sativa, Raphanus Sativus*] or Polyplant® Refirming [INCI: Coneflower, Asiatic Centella, Fucus, Fenugreek] marketed by Provital, Lanablue® [INCI: Sorbitol, Algae Extract] marketed by Atrium Innovations, Pepha®-Nutrix [INCI: Natural Nutrition Factor] marketed by Pentapharm, or plant extracts containing isoflavones or else at least one synthetic compound, extract or product coming from a biofermetation process with refirming, rethickening and/or restructuring activity, such as for example and in a non-limiting sense, Biopeptide EL™ [INCI: Palmitoyl Oligopeptide], Biopeptide CL™ [INCI: Palmitoyl Oligopeptide], Vexel® [INCI: Water (Aqua), Propylene Glycol, Lecithin, Caffeine, Palmitoyl Carnitine], Matrixyl® [INCI: Palmitoyl Pentapeptide-3], Matrixyl 3000® [INCI: Palmitoyl Tetrapeptide-3, Palmitoyl Oligopeptide] or Bio-Bustyl™ [INCI: Glyceryl Polymethacrylate, Rahnella Soy Protein Ferment, Water (Aqua), Propylene Glycol, Glycerin, PEG-8, Palmitoyl Oligopeptide] marketed by Sederma, Dermosaccharides® HC [INCI: Glycerin, Water (Aqua), Glycosaminoglycans, Glycogen], Aglycal® [INCI: Mannitol, Cyclodextrin, Glycogen, *Aratostaphylos Uva Ursi* Leaf Extract], Cytokinol® LS [INCI: Hydrolyzed Casein, Hydrolyzed Yeast Protein, Lysine HCL] or Firmiderm® LS9120 [INCI: *Terminalia Catappa* Leaf extract, *Sambucus Negra* Flower Extract, PVP, Tannic Acid] marketed by Laboratoires Serobiologiques/Cognis, Liftline® [INCI: Hydrolyzed wheat protein], Raffermine® [INCI: Hydrolyzed Soy Flour] or Ridulisse C® [Hydrolyzed Soy Protein] marketed by Silab, Serilesine® [INCI: hexapeptide-10] or Decorinyl™ [INCI: Tripeptide-10 Citrulline] marketed by Lipotec, Ursolisome® [INCI: Lecithin, Ursolic Acid, Atelocollagen, Xanthan Gum, Sodium Chondroitin Sulfate] or Collalift® [INCI: Hydrolyzed Malt Extract] marketed by Coletica/Engelhard, Syn®-Coll [INCI: Palmitoyl Tripeptide-5] marketed by Pentapharm, Hydriame® [INCI: Water (Aqua), Glycosaminoglycans, *Sclerotium* Gum] marketed by Atrium Innovations or IP2000 [INCI: Dextran, Trifluoroacetyl tripeptide-2] marketed by Institut Europeen de Biologie Cellulaire, among others.

Applications

Another aspect of the present invention refers to a cosmetic or pharmaceutical method for the treatment and/or care of those conditions, disorders and/or pathologies of the skin, mucosae and/or scalp in mammals, preferably in human beings, who benefit from MMP inhibition; comprising the administration of an effective amount of at least one peptide of general formula (I), stereoisomers thereof, mixtures thereof or cosmetically or pharmaceutically acceptable salts thereof, preferably in a cosmetic or pharmaceutical composition containing them. The present invention also provides a cosmetic or pharmaceutical method to inhibit MMPs, preferably skin, mucosae and/or scalp MMPs.

Likewise, the present invention provides a cosmetic or pharmaceutical method for treatment and/or care of those conditions, disorders and/or pathologies of the skin, mucosae and/or scalp which are caused by MMP overexpression or by an increase in the MMP activity, comprising the application on skin, mucosae and/or scalp or the oral or parenteral administration of a cosmetic or pharmaceutical composition containing at least one peptide of the invention, stereoisomers thereof, mixtures thereof or cosmetically or pharmaceutically acceptable salts thereof.

Preferably, among the conditions, disorders and/or pathologies of the skin, mucosae and/or scalp to be treated and/or cared caused by MMP overexpression or by an increase of MMP activity, there are included acne, rosacea, psoriasis, dermatitis, atopic dermatitis, eczema, sensitive skins, gingivitis, periodontitis, skin cancer, tumor invasions, aging skin, photoaging skin, wrinkles, expression wrinkles, stretch marks, keloids, hypertrophic scars, cellulitis, orange peel skin, tumor metastasis, ulcers, diabetic ulcers, telangiectasia, cuperosis, varicose veins, eye dark circles, bags under the eye, alopecia and hair loss.

Compositions containing the peptides of the present invention, stereoisomers thereof, mixtures thereof or the cosmetically or pharmaceutically acceptable salts thereof can be applied on skin, mucosae and/or scalp or be orally or parenterally administrated, as required to treat and/or care for a condition, disorder and/or pathology.

Application or administration frequency can vary widely, depending on each individual's needs; there being suggested an application or administration range from once a month up to ten times a day, preferably from once a week up to four times a day, more preferably from three times a week up to three times a day, even more preferably, once or twice a day.

An additional aspect of the present invention refers to the use of at least one peptide of general formula (I), stereoisomers thereof, mixtures thereof or cosmetically or pharmaceutically acceptable salts thereof, in the preparation of a cosmetic or pharmaceutical composition for the treatment and/or care of skin, mucosae and/or scalp.

Additionally, the present invention refers to the use of at least one peptide of general formula (I), stereoisomers thereof, mixtures thereof or cosmetically or pharmaceutically acceptable salts thereof, in the preparation of a cosmetic or pharmaceutical composition for MMP inhibition, preferably skin, mucosae and/or scalp MMPs.

Likewise, another aspect of the present invention refers to the use of at least one peptide of general formula (I), stereoisomers thereof, mixtures thereof or cosmetically or pharmaceutically acceptable salts thereof, in the preparation of a cosmetic or pharmaceutical composition for the treatment and/or care of skin, mucosae and/or those conditions, disorders and/or pathologies of the scalp caused by a MMP overexpression or by an increased MMP activity. Preferably, cosmetic or pharmaceutical compositions are created to treat and/or care those skin, mucosae and/or scalp areas affected by acne, rosacea, psoriasis, dermatitis, atopic dermatitis, eczema, sensitive skins, gingivitis, periodontitis, skin cancer, tumor invasions, aging skin, photoaging skin, wrinkles, expression wrinkles, stretch marks, keloids, hypertrophic scars, cellulitis, orange peel skin, tumor metastasis, ulcers, diabetic ulcers, telangiectasia, cuperosis, varicose veins, eye dark circles, bags under the eyes, alopecia and hair loss.

According to another important aspect, the present invention refers to the use of a peptide of general formula (I) in the preparation of a cosmetic or pharmaceutical composition for skin treatment aiming at reducing, delaying and/or preventing aging and photoaging signs.

In an additional embodiment, the present invention refers to the use of at least one of the peptides of general formula (I), stereoisomers thereof, mixtures thereof or cosmetically or pharmaceutically acceptable salts thereof, in the preparation of a cosmetic or pharmaceutical composition for oral treatment or hygiene. Preferably, the cosmetic or pharmaceutical composition is used for gingivitis and periodontitis treatment or prevention. Oral hygiene cosmetic or pharmaceutical composition examples include toothpaste, oral elixirs for mouth rinsing or chewing gum, among others.

An additional aspect of the present invention refers to the use of at least one of the peptides of general formula (I), stereoisomers thereof, mixtures thereof or cosmetically or pharmaceutically acceptable salts thereof, in the preparation of a cosmetic or pharmaceutical composition for hair treatment or hygiene. Preferably, the cosmetic or pharmaceutical composition is employed for alopecia and hair loss treatment or prevention. Hair hygiene cosmetic or pharmaceutical composition examples include shampoo, hair conditioners, hair lotions, hair tonics or scalp masks, among others.

Another aspect of the present invention refers to the use of at least one of the peptides of general formula (I), stereoisomers thereof, mixtures thereof or cosmetically or pharmaceutically acceptable salts thereof, in the preparation of a cosmetic or pharmaceutical composition for body treatment or hygiene.

The following specific examples are useful in illustrating the nature of the present invention. These examples are solely included for illustrative purposes and are not to be interpreted as limitations to the herein claimed invention.

EXAMPLES

General Methodology

All reagents and solvents are synthetic quality and are used without any additional treatment.

Abbreviations

The abbreviations used for amino acids follow the IUPAC-IUB Commission on Biochemical Nomenclature specified in *Eur. J. Biochem.* (1984) 138:9-37 and en *J. Biol. Chem.* (1989) 264:633-673.

Ac, acetyl; All, alyl; Alloc, alyloxycarbonyl; AM, 2-[4-aminomethyl (2,4 dimethoxyphenyl)] acid; Arg, arginine; Asn, asparagine; Boc, terc-butyloxycarbonyl; Bzl, benzyl; Cbz, benzyloxycarbonyl; cHex, cyclohexyl; Cit, citrulline; ClTrt-®, 2-chlorotrityl resin; cps, centipoise; C-terminal, carboxy-terminal; DCM, dichloromethane; DIEA, N,N-diisopropyllamine; DIPCDI, N,N'-diisopropylcarbodiimide; DMF, N,N-dimethylformamide; Dnp, 2,4-dinitrophenyl; DPPC, dipalmitoylphosphatidylcholine; equiv, equivalent; ESI-MS, electrospray ionization mass spectometry; Fmoc, 9-fluorenilmethyloxycarbonyl; His, histidine; HOAt, 1-hydroxybenzotriazole; HOBt, 1-hydroxybenzotriazole; HPLC, high-performance liquid chromatography; INCI, International Nomenclature of Cosmetic Ingredients; MBHA, resin p-metalbenzhydrylamine resin; MeCN, acetonitryl; MeOH, methanol; mLV, multilaminar vesicles; MMP, matrix metalloproteases; Mtr, 4-methoxy-2,3,6 trimethylbenzenesulfonyl; Mtt, methyltrityl; N-terminal, amino-terminal; PAL, 5-(4-aminomethyl-3,5-dimethoxyphenoxy) valeric acid; Palm, palmitoyl; Pbf, 2,2,4,6,7-pentamethyldihydrobenzofuran-5-sulfonil; Pmc, 2,2,5,7,8-pentamethyl-croman-6-sulfonic; pNZ, P-nitrobenzyloxycarbonyl;®, resin; tBu, terc-butyl; Teoc, 2-(trimethylsilyl)ethoxycarbonyl; TFA, trifluoroacetic acid; THF, tetrahydrofuran; TIMP, tissue inhibitor of metalloproteases matrix; TIS, triisopropylsilane; Tos, para-toluenesulfonyl or tosyl; Troc, 2,2,2-tricloroethyloxicarbonyl; Trt, triphenylmethyl or trityl; ULV, unilaminar vesicles; UV, ultraviolet; Xan, xanthyl.

Chemical Synthesis

All synthetic processes are performed with polypropylene syringes equipped with porous polyethylene discs or in Pyrex® reactors equipped with a porous plate. Soluble solvents and reagents are eliminated by suction. Fmoc group elimination is carried out with piperidine-DMF (2:8, v/v) (1×1 min, 1×5 min; 5 mL/g resin) [Lloyd-Williams P., Albericio F. and Giralt, E. (1997) *"Chemical Approaches to the Synthesis of Peptides and Proteins"* CRC, Boca Raton, Fla., USA].

Washings between unprotection, coupling and again unprotection stages have been carried out with DMF (3×1 min) using 10 mL solvent/g resin each time. Coupling reactions have been carried out with 3 mL solvent/g resin. Coupling control is carried out by ninhydrin test [Kaiser E., Colescott R. L., Bossinger C. D. and Cook P. I. (1970) *"Color test for detection of free terminal amino groups in the solid-phase synthesis of peptides"* Anal. Biochem. 34:595-598]. All synthetic transformations and washing have been carried out at room temperature.

Example 1

Obtaining Fmoc-AA$_1$-AA$_2$-AA$_3$-AA$_4$-O-2-ClTrt-®

3.5 g Fmoc-L-Cit-OH were added (8.8 mmol, 1 equiv), dissolved in 55 mL DCM, then 1.3 mL DIEA (7.6 mmol, 0.86 equiv) were added on the dried 2-chlorotrityl resin (5.5 g, 8.8 mmol). That solution was left in agitation during 5 min, after which 2.5 mL DIEA were added (14.6 mmol, 1.66 equiv). Then, it reacted during 40 min. Remaining chloride groups were blocked by treating them with 4.4 mL of MeOH.

Fmoc N-terminal group was unprotected as described in the general methods and 13.63 g Fmoc-L-His(Trt)-OH or 14.27 g Fmoc-L-Arg(Pbf)-OH (22 mmol, 2.5 equiv) were incorporated the peptidyl-resin in presence of DIPCDI (3.39 mL, 22 mmol, 2.5 equiv) and HOBt (3.37 g, 22 mmol, 2.5 equiv) using DMF as solvent during one hour. Afterwards, the resin was washed as described in the general methods and the Fmoc group unprotection treatment was repeated so as to incorporate the subsequent amino acid. Following the described protocols, 13.63 g Fmoc-L-His(Trt)-OH or 13.13 g Fmoc-L-Asn(Trt)-OH (22 mmol, 2.5 equiv) and 14.27 g of Fmoc-L-Arg(Pbf)-OH (22 mmol, 2.5 equiv) were sequentially coupled in presence of each 37 g HOBt (22 mmol, 2.5 equiv) and 3.39 mL DIPCDI (22 mmol, 2.5 equiv) coupling.

Once the synthesis was over, peptidyl-resins were washed with DCM (5×3 min) and dried by nitrogen flow.

Example 2

Prophetic

Obtaining Fmoc-AA$_1$-AA$_2$-AA$_3$-AA$_4$-AM-MBHA-®

6.85 g Fmoc-AM-MBHA resin of functionalization 0.73 mmol/g (5 mmol) are treated with piperidine-DMF, according to the described protocol so as to eliminate the Fmoc group. 9.9 g Fmoc-L-Cit-OH (25 mmol, 5 equiv) are added on the unprotected resin in presence of DIPCDI (3.85 mL, 25 mmol, 5 equiv) and HOBt (3.85 g, 25 mmol, 5 equiv) using DMF as solvent during 1 hour.

The resin is later washed as described in the general methods and the Fmoc group unprotection treatment is repeated so as to incorporate the subsequent amino acid. According to the described protocols, 15.49 g Fmoc-L-His(Trt)-OH or 16.22 g Fmoc-L-Arg(Pbf)-OH (25 mmol, 5 equiv), 15.49 g Fmoc-L-His(Trt)-OH or 14.92 g Fmoc-L-Asn(Trt)-OH (25 mmol, 5 equiv) and 16.22 g Fmoc-L-Arg(Pbf)-OH (25 mmol, 5 equiv) are sequentially coupled in presence of each 3.85 g HOBt (25 mmol, 5 equiv) and 3.85 mL DIPCDI (25 mmol, 5 equiv) coupling.

Once the synthesis is over, peptidyl-resins are washed with DCM (5×3 min) and dried by nitrogen flow.

Example 3

Prophetic

Fmoc N-Terminal Protecting Group General Excision Process

Fmoc N-terminal Group was unprotected from peptidyl-resins obtained in example 1 as it is described in the general methods (20% piperidine in DMF, 1×5 min+1×20 min). Peptidyl-resins were washed with DMF (5×1 min), DCM (4×1 min), Diethyl ether (4×1 min) and vacuum dried. The same process could have been applied to the N-terminal group of the peptidyl resin obtained in prophetic example 2.

Example 4

Prophetic

R$_1$ Palmitoyl Group Introduction Process: Obtaining Palm-AA$_1$-AA$_2$-AA$_3$-AA$_4$-O-2-ClTrt-® and Palm-AA$_1$-AA$_2$-AA$_3$-AA$_4$-AM-MBHA-®

2.56 g of palmitic acid (10 mmol, 10 equiv) pre-dissolved in DMF (1 mL) are added on 1 mmol of the peptidyl-resins obtained in example 3, in presence of 1.53 g HOBt (10 mmol, 10 equiv) and 1.54 mL DIPCDI (10 mmol, 10 equiv). They are left to react during 15 hours, after which resins are washed with THF (5×1 min), DCM (5×1 min), DMF (5×1 min), MeOH (5×1 min), DMF (5×1 min), THF (5×1 min), DMF (5×1 min), DCM (4×1 min), ether (3×1 min), and vacuum dried.

Example 5

Prophetic

R$_1$ Acetyl Group Introduction Process: Obtaining Ac-AA$_1$-AA$_2$-AA$_3$-AA$_4$-O-2-ClTrt-® and Ac-AA$_1$-AA$_2$-AA$_3$-AA$_4$-AM-MBHA-®

1 mmol of the peptidyl-resins obtained in example 3 were treated with 25 equiv Acetic anhydride in presence of 25 equiv DIEA using 5 mL DMF as solvent. They were left to react during 30 min, after which peptidyl-resins were washed with DMF (5×1 min), DCM (4×1 min), diethyl ether (4×1 min) and vacuum dried.

Example 6

Prophetic

Polymeric Support Excision Process: Obtaining H-AA$_1$-AA$_2$-AA$_3$-AA$_4$-OH, Ac-AA$_1$-AA$_2$-AA$_3$-AA$_4$-OH, Palm-AA$_1$-AA$_2$-AA$_3$-AA$_4$-OH, H-AA$_1$-AA$_2$-AA$_3$-AA$_4$-NH$_2$, Ac-AA$_1$-AA$_2$-AA$_3$-AA$_4$-NH$_2$ and Palm-AA$_1$-AA$_2$-AA$_3$-AA$_4$-NH$_2$ 200 mg of dried peptidyl-resins obtained in example 5 were treated with 5 mL of TFA-TIS-H$_2$O (90:5:5) during 2 hours at room temperature with agitation. Filtrations were collected on 50 mL cold diethyl ether, filtered through polypropylene syringes equipped with porous polyethylene discs and washed 5 times with 50 mL diethyl ether. Final precipitates were vacuum dried.

HPLC analysis of the peptides obtained in gradients of MeCN (+0.07% TFA) in H$_2$O (+0.1% TFA) showed purity higher than 85% in all cases. The identity of the peptides obtained was confirmed by ES-MS. The same process could have been applied to the N-terminal group of the peptidyl resin obtained in prophetic examples 3 and 4.

Example 7

Prophetic

Polymeric Support Excision Process and Functionalization with Substituted R$_2$ Amine: Obtaining Ac-AA$_1$-AA$_2$-AA$_3$-AA$_4$-NH—(CH$_2$)$_{15}$—CH$_3$ Ac-AA$_1$-AA$_2$-AA$_3$-AA$_4$-OH peptides with completely protected side chains were obtained by treating 150 mg of Ac-AA$_1$-AA$_2$-AA$_3$-AA$_4$-O-2-ClTrt-® peptidyl-resins from example 6, previously vacuum dried in presence of KOH, with 3 mL of a 3% solution of TFA in DCM during 5 min. Filtrations were collected on 50 mL of cold diethyl ether and the treatment was repeated three times. Ethereal solutions were submitted to rotavoporation at room dryness and temperature, precipitates were resuspended in 50% MeCN in H$_2$O and lyophilisated. 10 mg of the obtained raw peptides are weighted, and 3 equiv hexadecylamine and 25 mL DMF anhydride are added. 2 equiv DIPCDI are added and left to react with magnetic agitation at 47° C. Reactions are controlled by HPLC through disappearance of the starting material, which are complete after 24-48 hours. Solvents to dryness are evaporated and coevaporated twice with DCM. The residues obtained [Ac-AA$_1$-AA$_2$-AA$_3$-AA$_4$-NH—(CH$_2$)$_{15}$—CH$_3$ with completely protected side chains] are resuspended in 25 mL of a mixture of TFA-DCM-anisole (49:49:2) and are left to react during 30 min at room temperature. 250 mL of cold diethyl ether are added, solvents are evaporated under reduced pressure and two additional coevaporations were done with ether. Residues are dissolved in a mixture of 50% MeCN in H$_2$O and lyophilisated.

Example 8

Prophetic

Collagenase Inhibition Trial

Peptides were resuspended in water in the presence of 0.5% DMSO. The trial was carried out in black microplates having 96 well and the EnzChek® Gelatinase/Collagenase Assay Kit (Molecular Probes) was used. To that end, peptides were preincubated at 2 mg/mL during 1 hour with 0.1 unit/mL of type IV collagenase at room temperature with moderate agitation, after said time fluorescein conjugated substrate (DQ™ Gelatin) was added to a final concentration of 25 μg/mL and reactions were incubated for 2 hours at room temperature with agitation and protected from light. The substrate, whose fluorescence is inhibited, is directed into collagenase releasing fluorescent fragments, monitored by florescence with a FLUOstar galaxy reader (BMG LabTechnologies), using 485 nm filters for excitation and 520 nm for emission.

Table 2 details those peptides whose collagenase inhibition values are higher than 25%. Inhibition values were normalized with respect to medium inhibition basal values.

TABLE 2

Collagenase activity inhibition percentage

| Compound | Inhibition % |
|---|---|
| Ac-L-Arg-L-His-L-His-L-Cit-OH | 60.6 |
| Ac-L-Arg-L-Asn-L-Arg-L-Cit-OH | 58.9 |

Example 9

Prophetic

MMP-1, MMP-2, MMP-3 and MMP-9 Inhibition

Human MMPs were reconstructed in 50 mM Tris-HCl, 150 mM NaCl, 5 mM CaCl$_2$, 0.2 mM NaN$_3$ at a 7.6 pH and activated by reaction with 10 mM of 4-aminophenylmercuric acetate (dissolved in 0.01M NaOH) at a 10:1 to 37° C. ratio for 4-6 h. Activated proteases (0.35 μg/mL) were preincubated with peptides to a final 0.5 mM concentration in a 96-well black microplate for 1 hour at room temperature. After preincubation, 25 μg/mL substrate (DQ™ Gelatin) were added to the wells and samples were incubated for 16 hours at room temperature and protected against the light. Released fluorescence by marked gelatin digestion was measured with an automated multiplate fluorescence reader, exciting at 485 nm and reading at 520 nm.

The results were corrected from basal fluorescent value in MMP and product absence and normalized with respect to control fluorescence. Table 3 details the best inhibition values for peptides.

TABLE 3

Human MMPs inhibited by the peptides of the invention

| | MMP-1 | MMP-2 | MMP-3 | MMP-9 |
|---|---|---|---|---|
| Ac-L-Arg-L-His-L-His-L-Cit-OH | 34.7 | 101.4 | 39.1 | 63.1 |
| Ac-L-Arg-L-Asn-L-Arg-L-Cit-OH | −37.0 | 78.7 | 21.9 | 69.5 |

Example 10

Prophetic

Cosmetic Composition Containing Palm-L-Arg-L-Asn-L-his-L-Cit-NH$_2$ Preparation

The following formulation was prepared as described in the present invention:

| INGREDIENT (INCI nomenclature) | | WEIGHT % |
|---|---|---|
| A | MINERAL OIL | 8.0 |
| A | STEARIC ACID | 2.4 |
| A | CETEARYL ALCOHOL | 1.6 |
| A | BEESWAX | 0.8 |
| B | GLYCERINE | 2.4 |
| B | AQUA (WATER) | 63.4 |
| C | CARBOMER | 0.3 |
| C | TRIETHANOLAMINE | 0.9 |
| D | AQUA (WATER) | 15.0 |
| D | Palm-L-Arg-L-Asn-L-His-L-Cit-NH$_2$(0.01%) | 5.0 |
| D | LECITHIN | 0.4 |

Phase A components are weighed in a big enough reactor and the mixture is heated at 80° C. so as to melt the waxes. Phase B components are weighed in an adequate recipient for the whole content and heated at 70° C. Phase A is slowly added to phase B under intense agitation, and phase C is later added to that mixture under agitation. After the addition, it is left to cool with soft agitation and when the mixture is at room temperature an aqueous solution of Palm-L-Arg-L-Asn-L-His-L-Cit-NH$_2$ and lecithin is added, homogenized and pH is corrected with triethanolamine.

The pH obtained from the cream is 6-7 and viscosity 10.000-15.000 cps (6/50).

Example 11

Prophetic

Liposomes Containing Ac-L-Arg-L-his-L-his-L-Cit-OH Preparation

Dipalmitoylphosphatidylcholine (DPPC) is weighed and dissolved in chloroform. The solvent is vacuum evaporated until obtaining a fine phospholipid layer and said layer is hydrated by treatment at 55° C. with a peptide aqueous solution to the desired concentration (containing Phenonip®), and MLV liposomes are obtained. ULV liposomes are obtained by submerging MLV liposomes in an ultrasound bath at 55° C. during 2-minute 8 cycles in 5 minutes intervals. ULV liposomes size is reduced by passing them through a high pressure extrusion system.

| INGREDIENT (INCI nomenclature) | WEIGHT % |
|---|---|
| PHOSPHATIDYLCHOLINE | 4.0 |
| Ac-L-Arg-L-His-L-His-L-Cit-OH | 0.2 |
| PHENOXYETHANOL, METHYLPARABEN, ETHYLPARABEN, BUTYLPARABEN, PROPYLPARABEN, ISOBUTYLPARABEN | 0.50 |
| AQUA (WATER) | c.s.p. 100 |

Example 12

Prophetic

Facial Cream Composition Containing H-L-Arg-L-his-L-Arg-L-Cit-NH$_2$

Preparation

Mix Phase A components and heat at 70° C.

Mix Phase B components and heat at 70° C.

Add Phase C on Phase B agitating with homogenizer (Silverson) during 5 minutes.

Add Phase A little by little into the mixture of phases B and C with homogenizer keeping homogenization for 5 minutes.

Initiate cooling up to 30-35° C. with soft agitation. Add phase D at 50° C. Keep agitation. Add previously solubilised Phases E and F at 35-38° C.

| INGREDIENT (INCI Nomenclature) | | WEIGHT % |
|---|---|---|
| A | BUTYROSPERMUM PARKII | 3.5-4.5 |
| A | CETEARYL ETHYLHEXANOATE | 3-5 |
| A | GLYCERYL STEARATE S.E. | 1.5-2.5 |
| A | SQUALANE | 0.5-1 |
| A | PEG-100 STEARATE | 1 |
| A | POLYSORBATE 60 | 0.30 |
| A | CETYL PALMITATE | 1.5-2.5 |
| A | DIMETHICONE | 2.5-3.5 |
| A | CETEARYL ALCOHOL | 1.5-2.5 |
| A | PALMITIC ACID | 0.5 |
| B | AQUA (WATER) | 2 |
| B | GLYCERIN | 1.5-2.5 |
| B | BUTYLENE GLYCOL | 1-3 |
| B | MANNITOL | 0.5-1.5 |
| B | HYDROGENATED LECITHIN | 0.5-1.5 |
| B | PROPYLENE GLYCOL | 0.5-1.5 |
| C | CARBOMER | 0.4 |
| C | ETHYLHEXYL PALMITATE | 1.5-2.5 |
| D | TROMETHAMINE | 0.4 |
| D | AQUA (WATER) | 1 |
| E | PRESERVATIVES | q.s. |
| F | H-L-Arg-L-His-L-Arg-L-Cit-NH$_2$ | 0.10 |
| F | AQUA (WATER) | c.s.p.100 |

Example 13

Prophetic

Liposome Gel Composition Preparation Containing Ac-L-Arg-L-his-L-his-L-Cit-OH

The liposomes of example 11 are spread in water with preservatives (EDTA, imidazolidinyl urea and Phenonip®) under soft agitation. Hispagel® 200 [INCI: Aqua, glycerin, glyceryl polyacrylate] is added and softly agitated until a homogenous mixture is obtained.

| INGREDIENT (INCI nomenclature) | WEIGHT % |
|---|---|
| LIPOSOMES CONTAINING Ac-L-Arg-L-His-L-His-L-Cit-OH (1%) | 10.00 |
| DISODIUM EDTA | 0.15 |
| IMIDAZOLIDINYL UREA | 0.10 |
| PHENOXYETHANOL, METHYLPARABEN, ETHYLPARABEN, BUTYLPARABEN, PROPYLPARABEN, ISOBUTYLPARABEN | 0.50 |
| AQUA (WATER) | 29.25 |
| AQUA (WATER), GLYCERIN, GLYCERYL POLYACRYLATE | 60.00 |

Example 14

Prophetic

Mixed Micelles Composition Containing Ac-L-Arg-L-his-L-his-L-Cit-OH Preparation

| | INGREDIENT (INCI nomenclature) | WEIGHT % |
|---|---|---|
| A | AQUA (WATER) | c.s.p.100 |
| A | PHENOXYETHANOL | 0.5 |
| A | CAPRILYL GLYCOL | 0.5 |
| A | POTASIUM SORBATE | 0.3 |
| B | AQUA (WATER), PSEUDOALTEROMONAS FERMENT EXTRACT | 7.5 |
| B | Ac-L-Arg-L-His-L-His-L-Cit-OH | 0.025 |
| B | AQUA (WATER), PENTAPEPTIDE-18 | 20 |
| B | LECITHIN | 4.0 |
| C | XANTHAN GUM | 0.4 |
| D | AQUA (WATER), CAPRILYUCAPRYL GLUCOSIDE | 30 |

In the right container for the complete sample, phase A ingredients are weighed and lightly heated at 30° C. to help dissolve part of the preservatives. After that, phase B components are added and homogenized under moderate agitation.

Then, phase C is added under continuous agitation, after which phase D is added with slow agitation so as not to produce foam.

pH is adjusted to 5.5-6.5.

Example 15

Prophetic

Composition Containing Ac-L-Arg-L-his-L-his-L-Cit-OH for the Treatment and/or Prevention of Stretch Marks In the right container for the complete sample, phase A components are weighed and lightly heated at 30° C. to help dissolve part of the preservatives. After that, phase B components are mixed and added onto phase A and the composition is homogenized under moderate agitation.

| INGREDIENT (INCI nomenclature) | | WEIGHT % |
|---|---|---|
| A | GLYCERIN | 50 |
| A | PHENOXYETHANOL | 0.50 |
| A | CAPRILYL GLYCOL | 0.50 |
| B | AQUA (WATER), PSEUDOALTEROMONAS FERMENT EXTRACT | 7.50 |
| B | Ac-L-Arg-L-His-L-His-L-Cit-OH | 0.025 |
| B | AQUA (WATER) | c.s.p.100 |

Example 16

Prophetic

Hair Lotion Composition Containing
Ac-L-Arg-L-Asn-L-his-L-Cit-NH$_2$

| INGREDIENT (INCI nomenclature) | | WEIGHT % |
|---|---|---|
| A | ALCOHOL DENAT. | 50-60 |
| A | PANTHENOL | 0.05-0.15 |
| A | ZINC RICINOLEATE | 0.05-0.10 |
| A | FRAGRANCE | 0.02 |
| B | AQUA (WATER) | c.s.p.100 |
| B | Ac-L-Arg-L-Asn-L-His-L-Cit-NH$_2$ | 0.01 |

Preparation:

Mix Phase A components.

Mix Phase B components.

Slowly add Phase B onto Phase A with agitation until complete homogenization.

Example 17

Prophetic

Collutory Composition Containing
Ac-L-Arg-L-his-L-his-L-Cit-OH

Components are mixed until complete homogenization.

| INGREDIENT (INCI nomenclature) | WEIGHT % |
|---|---|
| Ac-L-Arg-L-His-L-His-L-Cit-OH | 0.10 |
| SODIUM SACCARIN | 0.01-0.03 |
| SORBITOL | 4-6 |
| PROPYLENE GLYCOL | 8-12 |
| PEG-60 HYDROGENATED CASTOR OIL | 1-3 |
| AQUA (WATER) | c.s.p.100 |

The invention claimed is:

1. A peptide of general formula (I)

$$R_1\text{-}AA_1\text{-}AA_2\text{-}AA_3\text{-}AA_4\text{-}R_2 \qquad (I)$$

stereoisomers thereof, mixtures of stereoisomers thereof, or the cosmetically or pharmaceutically acceptable salts thereof, wherein:

$AA_1$ is -Arg-;

$AA_2$ is selected from the group consisting of -His- and -Asn-;

$AA_3$ is selected from the group consisting of -His- and -Arg-;

$AA_4$ is -Cit-;

each of $AA_1$, $AA_2$, $AA_3$, and $AA_4$ is independently selected from L- and D-configurations and mixtures thereof;

$R_1$ is selected from the group consisting of H, substituted or non-substituted non-cyclic aliphatic groups, substituted or non-substituted alicyclyl, substituted or non-substituted heterocyclyl, substituted or non-substituted heteroarylalkyl, substituted or non-substituted aryl, substituted or non-substituted aralkyl, and $R_5$—CO—; and $R_2$ is selected from the group consisting of —$NR_3R_4$, —$OR_3$ and —$SR_3$; wherein $R_3$ and $R_4$ are independently selected from the group consisting of H, substituted or non-substituted non-cyclic aliphatic groups, substituted or non-substituted alicyclyl, substituted or non-substituted heterocyclyl, substituted or non-substituted heteroarylalkyl, substituted or non-substituted aryl and substituted or non-substituted aralkyl, wherein $R_5$ is selected from the group consisting of H, substituted or non-substituted non-cyclic aliphatic groups, substituted or non-substituted alicyclyl, substituted or non-substituted aryl, substituted or non-substituted aralkyl, substituted or non-substituted heterocyclyl and substituted or non-substituted heteroarylalkyl.

2. The peptide according to claim 1, wherein $R_1$ is H, or a $R_5$—CO— group wherein $R_5$ is selected from the group consisting of substituted or non-substituted $C_1$-$C_{24}$ alkyl, substituted or non-substituted $C_2$-$C_{24}$ alkenyl, substituted or non-substituted $C_2$-$C_{24}$ alkynyl, substituted or non-substituted $C_3$-$C_{24}$ cycloalkyl, substituted or non-substituted $C_5$-$C_{24}$ cycloalkenyl, substituted or non-substituted $C_5$-$C_{24}$ cycloalkynyl, substituted or non-substituted $C_6$-$C_{30}$ aryl, substituted or non-substituted $C_7$-$C_{24}$ aralkyl, substituted or non-substituted 3 to 10 member heterocyclyl and substituted or non-substituted heteroarylalkyl with from 2 to 24 carbon atoms and from 1 to 3 atoms different from carbon and an alkyl chain of 1 to 6 carbon atoms.

3. The peptide according to claim 2, wherein $R_1$ is selected from the group consisting of H, acetyl, tert-butanoyl, hexanoyl, 2-methylhexanoyl, cyclohexanecarboxyl, octanoyl, decanoyl, lauroyl, myristoyl, palmitoyl, stearoyl, oleoyl and linoleoyl.

4. The peptide according to claim 1, wherein $R_2$ is —$NR_3R_4$ or —$OR_3$, wherein $R_3$ and $R_4$ are independently selected from the group consisting of H, substituted or non-substituted $C_1$-$C_{24}$ alkyl, substituted or non-substituted $C_2$-$C_{24}$ alkenyl, substituted or non-substituted $C_2$-$C_{24}$ alkynyl, substituted or non-substituted $C_3$-$C_{24}$ cycloalkyl, substituted or non-substituted $C_5$-$C_{24}$ cycloalkenyl, substituted or non-substituted $C_5$-$C_{24}$ cycloalkynyl, substituted or non-substituted $C_6$-$C_{30}$ aryl, substituted or non-substituted $C_7$-$C_{24}$ aralkyl, substituted or non-substituted 3 to 10 member heterocyclyl and substituted or non-substituted heteroarylalkyl with from 2 to 24 carbon atoms and from 1 to 3 atoms different from carbon and an alkyl chain of 1 to 6 carbon atoms.

5. The peptide according to claim 4, wherein $R_3$ and $R_4$ are selected from the group consisting of H, methyl, ethyl, hexyl, dodecyl and hexadecyl.

6. The peptide according to claim 1, wherein $AA_2$ is -His- and $AA_3$ is -His-.

7. The peptide according to claim 1, wherein $AA_2$ is -Asn- and $AA_3$ is -Arg-.

8. The peptide according to claim 1, wherein $R_1$ is H, acetyl, lauroyl, myristoyl or palmitoyl, $AA_1$ is -L-Arg-, $AA_2$ is -L-His-, $AA_3$ is -L-His-, $AA_4$ is -L-Cit-, and $R_2$ is —$NR_3R_4$ or —$OR_3$ wherein $R_3$ and $R_4$ are independently selected from H, methyl, ethyl, hexyl, dodecyl and hexadecyl groups.

9. The peptide according to claim 1, wherein $R_1$ is H, acetyl, lauroyl, myristoyl or palmitoyl, $AA_1$ is -L-Arg-, $AA_2$ is -L-Asn-, $AA_3$ is -L-Arg-, $AA_4$ is -L-Cit-, and $R_2$ is —$NR_3R_4$ or —$OR_3$ wherein $R_3$ and $R_4$ are independently selected from H, methyl, ethyl, hexyl, dodecyl and hexadecyl groups.

10. A process for obtaining a peptide of general formula (I), stereoisomers thereof, mixtures thereof or the cosmetically or pharmaceutically acceptable salts thereof as defined in claim 1, wherein said process comprises synthesizing said peptide on solid phase or in solution.

11. A cosmetic or pharmaceutical composition comprising a cosmetically or pharmaceutically effective amount of at least one peptide of general formula (I), stereoisomers thereof, mixtures thereof or the cosmetically or pharmaceutically acceptable salts thereof, as defined in claim 1, and at least one cosmetically or pharmaceutically acceptable excipient or adjuvant.

12. The cosmetic or pharmaceutical composition according to claim 11, wherein the peptide of general formula (I), stereoisomers thereof, mixtures thereof or the cosmetically or pharmaceutically acceptable salts thereof is/are incorporated into a cosmetic or pharmaceutical delivery system and/or a sustained release system selected from group consisting of liposomes, mixed liposomes, millicapsules, microcapsules, nanocapsules, sponges, cyclodextrins, vesicles, micelles, surfactant mixed micelles, phospholipid-surfactant mixed micelles, millispheres, microspheres, nanospheres, lipospheres, microemulsions, nanoemulsions, milliparticles, microparticles, nanoparticles and solid lipidic nanoparticles and/or is absorbed on a solid organic polymer or cosmetically or pharmaceutically acceptable solid support, selected from the group consisting of talcum powder, bentonite, silica, starch and maltodextrin.

13. The cosmetic or pharmaceutical composition according to claim 11, wherein said composition is selected from the group consisting of creams, multiple emulsions, anhydrous compositions, aqueous dispersions, oils, milks, balsams, foams, lotions, gels, cream gels, hydroalcoholic solutions, hydroglycolic solutions, liniments, saline solutions, soaps, shampoos, conditioners, sera, unguents, mousses, ointments, powders, bars, pencils, sprays, aerosols, capsules, gelatin capsules, tablets, sugar coated tablets, powders, granulated forms, chewing gum, solutions, suspensions, emulsions, syrups, polysaccharides films, jellies and gelatins.

14. The cosmetic or pharmaceutical composition according to claim 11, wherein said composition is a product selected from the group consisting of under-eye removers, makeup foundations, makeup remover lotions, milk makeup remover, eye shadows, lipsticks, lip glosses and powders.

15. The cosmetic or pharmaceutical composition according to claim 11, wherein the peptide of general formula (I), stereoisomers thereof, mixtures thereof or the cosmetically or pharmaceutically acceptable salts thereof is/are incorporated into a fabric, a non-woven fabric or a medical device.

16. A cosmetic or pharmaceutical method for the treatment and/or care of skin, mucosae and/or scalp, comprising the administration of an effective amount of at least one peptide of general formula (I)

$$R_1\text{-}AA_1\text{-}AA_2\text{-}AA_3\text{-}AA_4\text{-}R_2 \qquad (I),$$

stereoisomers thereof, mixtures of stereoisomers thereof, or the cosmetically or pharmaceutically acceptable salts thereof, to the skin, mucosae and/or scalp, wherein said treatment and/or care includes inhibiting at least one skin, mucosae and/or scalp matrix metalloprotease selected from the group consisting of human MMP-1, MMP-2, MMP-3 and MMP-9, wherein:

$AA_1$ is -Arg-;

$AA_2$ is selected from the group consisting of -His- and -Asn-;

$AA_3$ is selected from the group consisting of -His- and -Arg-;

$AA_4$ is -Cit-;

each of $AA_1$, $AA_2$, $AA_3$, and $AA_4$ is independently selected from L- and D-configurations and mixtures thereof;

$R_1$ is selected from the group consisting of H, substituted or non-substituted non-cyclic aliphatic groups, substituted or non-substituted alicyclyl, substituted or non-substituted heterocyclyl, substituted or non-substituted heteroarylalkyl, substituted or non-substituted aryl, substituted or non-substituted aralkyl, and $R_5$—CO—;

$R_2$ is selected from the group consisting of —$NR_3R_4$, —$OR_3$ and —$SR_3$; wherein $R_3$ and $R_4$ are independently selected from the group consisting of H, substituted or non-substituted non-cyclic aliphatic groups, substituted or non-substituted alicyclyl, substituted or non-substituted heterocyclyl, substituted or non-substituted heteroarylalkyl, substituted or non-substituted aryl and substituted or non-substituted aralkyl; and $R_5$ is selected from the group consisting of H, substituted or non-substituted non-cyclic aliphatic groups, substituted or non-substituted alicyclyl, substituted or non-substituted aryl, substituted or non-substituted aralkyl, substituted or non-substituted heterocyclyl, and substituted or non-substituted heteroarylalkyl.

17. The cosmetic or pharmaceutical method according to claim 16, wherein said administration is topical or transdermal administration.

18. The cosmetic or pharmaceutical method according to claim 16, wherein the administration includes administering the effective amount to the hair and/or scalp for scalp and/or hair hygiene.

19. The cosmetic or pharmaceutical method according to claim 16, wherein the administration includes administering the effective amount to the skin for skin hygiene.

20. The cosmetic or pharmaceutical composition, according to claim 11, wherein said composition additionally comprises a cosmetically or pharmaceutically effective amount of at least one selected active agent consisting of agents inhibiting matrix metalloelastases, agents stimulating or inhibiting melanin synthesis, whitening or depigmenting agents, propigmenting agents, self-tanning agents, anti-age agents, NO-synthase inhibiting agents, antioxidant agents, free radicals scavengers and/or anti-atmospheric pollution agents, anti-glycation agents, emulsifying agents, emollients, organic solvents, liquid propellants, skin conditioners, substances retaining moisture, alphahydroxyacids, betahydroxyacids, moisturizers, epidermic hydrolytic enzymes, vitamins, pigments or colorants, dyes, gelling polymers, thickeners, surfactants, softeners, anti-wrinkle agents, agents capable of reducing or treating bags under the eyes, exfoliating agents, antimicrobial agents, fungicide agents, fungistatic agents, bactericide agents, bacteriostatic agents, agents stimulating the synthesis of dermal or epidermal macromolecules and/or agents capable of preventing or inhibiting their degradation, agents stimulating collagen synthesis, agents stimulating elastin synthesis, agents stimulating decorine synthesis, agents stimulating laminin synthesis, agents stimulating defensin synthesis, agents stimulating chaperone synthesis, agents stimulating aquaporin synthesis, agents stimulating hyaluronic acid synthesis, agents stimulating the synthesis of lipids and components of the stratum corneum, agents stimulating the synthesis of ceramides, agents inhibiting collagen degradation, agents inhibiting elastin degradation, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents inhibiting acetylcholinesterase, dermorelaxing agents, agents stimulating glycosaminoglycan synthesis, DNA repairing agents, DNA protecting agents, anti-itching agents, agents for the treatment and/or care of sensitive skin, firming agents, anti-stretch mark agents, astringent agents, agents regulating sebum production, agents stimulating lipolysis, anticellulitic agents, agents stimulating healing, coadjutant healing agents, agents stimulating reepithelizing, coadjutant reepithelizing agents, cytokine growth factors, calming agents, anti-inflammatory agents, agents acting on capillary circulation and/or microcirculation, agents stimulating angiogenesis, agents inhibiting vascular permeability, agents acting on cell metabolism, agents intended to improve the dermal-epidermal junction, agents inducing hair growth, agents inhibiting or delaying hair growth, preservatives, perfumes, chelating agent, plant extracts, essential oils, marine extracts, agents coming from a bio-fermentation process, mineral salts, cell extracts and sunscreens (organic or mineral photoprotecting agents that are active against ultraviolet A and/or B rays), or mixtures thereof.

* * * * *